United States Patent
Sun et al.

(10) Patent No.: US 12,083,185 B2
(45) Date of Patent: Sep. 10, 2024

(54) SMALL POLYMERIC CARRIERS FOR DELIVERY OF AGENTS

(71) Applicant: University of Pittsburgh—Of the Commonwealth System of Higher Education, Pittsburgh, PA (US)

(72) Inventors: Jingjing Sun, Pittsburgh, PA (US); Song Li, Mars, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 358 days.

(21) Appl. No.: 17/284,562

(22) PCT Filed: Oct. 11, 2019

(86) PCT No.: PCT/US2019/055766
§ 371 (c)(1),
(2) Date: Apr. 12, 2021

(87) PCT Pub. No.: WO2020/077170
PCT Pub. Date: Apr. 16, 2020

(65) Prior Publication Data
US 2021/0330808 A1    Oct. 28, 2021

Related U.S. Application Data

(60) Provisional application No. 62/744,928, filed on Oct. 12, 2018.

(51) Int. Cl.
| | | |
|---|---|---|
| *A61K 47/69* | (2017.01) | |
| *A61K 9/107* | (2006.01) | |
| *A61K 31/12* | (2006.01) | |
| *A61K 31/138* | (2006.01) | |
| *A61K 31/337* | (2006.01) | |
| *A61K 31/366* | (2006.01) | |
| *A61K 31/404* | (2006.01) | |
| *A61K 31/405* | (2006.01) | |
| *A61K 31/436* | (2006.01) | |
| *A61K 31/506* | (2006.01) | |
| *A61K 31/551* | (2006.01) | |
| *A61K 31/7068* | (2006.01) | |
| *A61K 38/13* | (2006.01) | |
| *A61K 47/54* | (2017.01) | |
| *A61K 47/58* | (2017.01) | |
| *A61K 47/60* | (2017.01) | |

(52) U.S. Cl.
CPC ........ *A61K 47/6907* (2017.08); *A61K 9/1075* (2013.01); *A61K 31/12* (2013.01); *A61K 31/138* (2013.01); *A61K 31/337* (2013.01); *A61K 31/366* (2013.01); *A61K 31/404* (2013.01); *A61K 31/405* (2013.01); *A61K 31/436* (2013.01); *A61K 31/506* (2013.01); *A61K 31/551* (2013.01); *A61K 31/7068* (2013.01); *A61K 38/13* (2013.01); *A61K 47/54* (2017.08); *A61K 47/542* (2017.08); *A61K 47/58* (2017.08); *A61K 47/60* (2017.08)

(58) Field of Classification Search
CPC .............. A61K 31/7068; A61K 31/706; A61K 47/6907; A61K 31/12; A61K 31/138; A61K 31/337; A61K 31/366; A61K 31/404; A61K 31/405; A61K 31/436; A61K 31/506; A61K 31/551; A61K 31/704; A61K 9/1075; A61K 38/13; A61K 47/54; A61K 47/542; A61K 47/58; A61K 47/60; A61K 45/06; A61K 2300/00
See application file for complete search history.

(56) References Cited

U.S. PATENT DOCUMENTS

| | | | |
|---|---|---|---|
| 5,521,290 A * | 5/1996 | Sivam ................ | C07D 207/404 530/391.5 |
| 5,763,548 A | 6/1998 | Matyjaszewski | |
| 5,789,487 A | 8/1998 | Matyjaszewski | |
| 5,807,937 A | 9/1998 | Matyjaszewski | |
| 5,945,491 A | 8/1999 | Matyjaszewski | |
| 6,111,022 A | 8/2000 | Matyjaszewski | |
| 6,121,371 A | 9/2000 | Matyjaszewski | |
| 6,124,411 A | 9/2000 | Matyjaszewski | |
| 6,162,882 A | 12/2000 | Matyjaszewski | |
| 6,407,187 B1 | 6/2002 | Matyjaszewski | |
| 6,512,060 B1 | 1/2003 | Matyjaszewski | |
| 6,538,091 B1 | 3/2003 | Matyjaszewski | |
| 6,541,580 B1 | 4/2003 | Matyjaszewski | |

(Continued)

FOREIGN PATENT DOCUMENTS

| | | |
|---|---|---|
| WO | WO199513059 A1 | 5/1995 |
| WO | WO2007086651 A1 | 8/2007 |

(Continued)

OTHER PUBLICATIONS

Lu et al., Macromol. Rapid Commun., 2016, 37, p. 2023-2029. (Year: 2016).*
Ren et al., RSC Adv., 2014, 4, p. 34729-34732. (Year: 2014).*
L. Rahib et al., Projecting cancer incidence and deaths to 2030: the unexpected burden of thyroid, liver, and pancreas cancers in the United States, Cancer Res. 74 (2014) 2913-2921.
H. Burris 3rd et al., Improvements in survival and clinical benefit with gemcitabine as first-line therapy for patients with advanced pancreas cancer: a randomized trial, J. Clin. Oncol. 15 (1997) 2403-2413.
L.A. Shipley et al., Metabolism and disposition of gemcitabine, and oncolytic deoxycytidine analog, in mice, rats, and dogs, Drug Metab. Dispos. 20 (1992) 849-855.
K.K. Frese et al., nab-Paclitaxel potentiates gemcitabine activity by reducing cytidine deaminase levels in a mouse model of pancreatic cancer, Cancer discovery 2 (2012) 260-269.

(Continued)

*Primary Examiner* — Jonathan S Lau
(74) *Attorney, Agent, or Firm* — BARTONY & ASSOCIATES, LLC

(57) ABSTRACT

A polymer includes a hydrophobic polymer backbone, a first plurality of pendant groups attached to the hydrophobic polymer backbone and including at least one group including a plurality of hydroxyl groups, and a second plurality of pendant groups attached to the hydrophobic polymer backbone and comprising at least one hydrophilic polymer.

42 Claims, 16 Drawing Sheets

(56) References Cited

U.S. PATENT DOCUMENTS

| | | | |
|---|---|---|---|
| 6,562,330 B1 | 5/2003 | Stratford | |
| 6,624,262 B2 | 9/2003 | Matyjaszewski | |
| 6,624,263 B2 | 9/2003 | Matyjaszewski | |
| 6,627,314 B2 | 9/2003 | Matyjaszewski | |
| 6,676,971 B2 | 1/2004 | Goupil | |
| 6,759,491 B2 | 7/2004 | Matyjaszewski | |
| 6,790,919 B2 | 9/2004 | Matyjaszewski | |
| 6,887,962 B2 | 5/2005 | Matyjaszewski | |
| 7,019,082 B2 | 3/2006 | Matyjaszewski | |
| 7,049,373 B2 | 5/2006 | Matyjaszewski | |
| 7,064,166 B2 | 6/2006 | Matyjaszewski | |
| 7,125,938 B2 | 10/2006 | Matyjaszewski | |
| 7,157,530 B2 | 1/2007 | Matyjaszewski | |
| 7,332,550 B2 | 2/2008 | Matyjaszewski | |
| 7,572,874 B2 | 8/2009 | Matyjaszewski | |
| 7,678,869 B2 | 3/2010 | Matyjaszewski | |
| 7,795,355 B2 | 9/2010 | Matyjaszewski | |
| 7,825,199 B1 | 11/2010 | Matyjaszewski | |
| 7,893,173 B2 | 2/2011 | Matyjaszewski | |
| 7,893,174 B2 | 2/2011 | Matyjaszewski | |
| 8,252,880 B2 | 8/2012 | Matyjaszewski | |
| 8,273,823 B2 | 9/2012 | Matyjaszewski | |
| 8,318,816 B2 | 11/2012 | Hoffman | |
| 8,349,410 B2 | 1/2013 | Huang | |
| 9,855,341 B2 | 1/2018 | Li | |
| 9,949,927 B2 | 4/2018 | Xu | |
| 10,172,795 B2 | 1/2019 | Gao | |
| 2009/0055944 A1 | 2/2009 | Korman | |
| 2011/0065807 A1 | 3/2011 | Radovic-Moreno | |
| 2011/0117024 A1 | 5/2011 | Sinko | |
| 2011/0229572 A1 | 9/2011 | Lewis | |
| 2012/0213854 A1 | 8/2012 | Fetzer | |
| 2012/0309780 A1 | 12/2012 | Kwon | |
| 2013/0244982 A1 | 9/2013 | Dahan | |
| 2014/0030350 A1 | 1/2014 | Ashrafi | |
| 2014/0155577 A1 | 6/2014 | Parquette | |
| 2015/0150888 A1 | 6/2015 | Resche-Rigon et al. | |
| 2015/0197585 A1 | 7/2015 | Epps, III | |
| 2017/0189560 A1 | 7/2017 | Popovtzer | |
| 2018/0214563 A1 | 8/2018 | Li | |
| 2018/0291134 A1 | 10/2018 | Gao | |

FOREIGN PATENT DOCUMENTS

| | | | |
|---|---|---|---|
| WO | WO2013152227 A1 | 10/2013 | |
| WO | WO2014080251 A1 | 5/2014 | |
| WO | WO2014093631 A1 | 6/2014 | |
| WO | WO2019204799 A1 | 10/2019 | |
| WO | WO2020077170 | 4/2020 | |

OTHER PUBLICATIONS

N. Awasthi et al., Comparative benefits of Nab-paclitaxel over gemcitabine or polysorbatebased docetaxel in experimental pancreatic cancer, Carcinogenesis 34 (2013) 2361-2369.

H. Meng et al., Use of a lipid-coated mesoporous silica nanoparticle platform for synergistic gemcitabine and paclitaxel delivery to human pancreatic cancer in mice, ACS Nano 9 (2015) 3540-3557.

L. Zitvogel et al., Immunological aspects of cancer chemotherapy, Nat. Rev. Immunol. 8 (2008) 59-73.

L. Apetoh et al., Toll-like receptor 4-dependent contribution of the immune system to anticancer chemotherapy andradiotherapy, Nat. Med. 13 (2007) 1050.

M.S. Sasso et al., Low dose gemcitabine-loaded lipid nanocapsules target monocytic myeloid-derived suppressor cells and potentiate cancer immunotherapy, Biomaterials 96 (2016) 47-62.

K.Thind et al., Immunotherapy in pancreatic cancer treatment: a new frontier, Therapeutic advances in gastroenterology 10 (2017) 168-194.

N. Martinez-Bosch et al., Immune Evasion in Pancreatic Cancer: from Mechanisms to Therapy, Cancers 10 (2018) 6.

C. Uyttenhove et al., Evidence for a tumoral immune resistance mechanism based on tryptophan degradation by indoleamine 2, 3-dioxygenase, Nat. Med. 9 (2003) 1269.

J. Godin-Ethier et al., Indoleamine 2, 3-dioxygenase expression in human cancers: clinical and immunologic perspectives, Clin. Cancer Res. 17 (2011) 6985-6991.

H.K. Koblish et al., Hydroxyamidine inhibitors of indoleamine-2, 3-dioxygenase potently suppress systemic tryptophan catabolism and the growth of IDO-expressing tumors, Mol. Cancer Ther. 9 (2010) 489-498.

N.Liu et al., Selective inhibition of IDO1 effectively regulates mediators of antitumor immunity, Blood 115 (2010) 3520-3530.

A. Witkiewicz et al., Expression of indoleamine 2, 3-dioxygenase in metastatic pancreatic ductal adenocarcinoma recruits regulatory T cells to avoid immune detection, J. Am. Coll. Surg. 206 (2008) 849-854.

D.H. Munn et al., Indoleamine 2, 3-dioxygenase and tumor-induced tolerance, The Journal of clinical investigation 117 (2007) 1147-1154.

D.H. Munn et al., IDO in the tumor microenvironment: inflammation, counterregulation, and tolerance, Trends Immunol. 37 (2016) 193-207.

A. Nayak et al., A Phase I study of NLG919 for adult patients with recurrent advanced solid tumors, Journal for Immunotherapy of cancer 2 (2014) P250.

Y. Chen et al., An immunostimulatory dual-functional nanocarrier that improves cancer immunochemotherapy, Nat. Commun. 7 (2016) 13443-13455.

H. Maeda et al., The EPR effect for macromolecular drug delivery to solid tumors: Improvement of tumor uptake, lowering of systemic toxicity, and distinct tumor imaging in vivo, Adv. Drug Delivery. Rev. 65 (2013) 71-79.

M.K.Danquah et al., Extravasation of polymeric nanomedicines across tumor vasculature, Adv. Drug Delivery. Rev. 63 (2011) 623-639.

F. Danhier et al., To exploit the tumor microenvironment: passive and active tumor targeting of nanocarriers for anti-cancer drug delivery, J. Control. Release 148 (2010) 135-146.

V.P. Chauhan et al., Strategies for advancing cancer nanomedicine, Nat. Mater. 12 (2013) 958-962.

H. Cabral et al., Accumulation of sub-100 nm polymeric micelles in poorly permeable tumours depends on size, Nat. Nanotechnol. 6 (2011) 815-823.

V.P. Chauhan et al., Normalization of tumour blood vessels improves the delivery of nanomedicines in a size-dependent manner, Nat. Nanotechnol. 7 (2012) 383-388.

K. Huang et al., Size-dependent localization and penetration of ultrasmall gold nanoparticles in cancer cells, multicellular spheroids, and tumors in vivo, ACS Nano 6 (2012) 4483-4493.

Z. Popovic et al., A nanoparticle size series for in vivo fluorescence imaging, Angew. Chem. 122 (2010) 8831-8834.

V.P. Chauhan et al., Fluorescent nanorods and nanospheres for real-time in vivo probing of nanoparticle shapedependent tumor penetration, Angewandte Chemie International Edition 50 (2011) 11417-11420.

J. Sun et al., A prodrug micellar carrier assembled from polymers with pendant farnesyl thiosalicylic acid moieties for improved delivery of paclitaxel, Acta Biomater. 43 (2016) 282-291.

R. Bruni et al., Ultrasmall polymeric nanocarriers for drug delivery to podocytes in kidney glomerulus, J. Control. Release 255 (2017) 94-107.

M. Vandana et al., Long circulation and cytotoxicity of PEGylated gemcitabine and its potential for the treatment of pancreatic cancer, Biomaterials 31 (2010) 9340-9356.

D. Chitkara et al., Self-assembling, amphiphilic polymer-gemcitabine conjugate shows enhanced antitumor efficacy against human pancreatic adenocarcinoma, Bioconjug. Chem. 24 (2013) 1161-1173.

J. Sun et al., Doxorubicin delivered by a redox-responsive dasatinib-containing polymeric prodrug carrier for combination therapy, J. Control. Release 258 (2017) 43-55.

M. Zauri et al., CDA directs metabolism of epigenetic nucleosides revealing a therapeutic window in cancer, Nature 524 (2015) 114-118.

(56) References Cited

OTHER PUBLICATIONS

N. Weizman et al., Macrophages mediate gemcitabine resistance of pancreatic adenocarcinoma by upregulating cytidine deaminase, Oncogene 33 (2014) 3812-3819.
T. Kammertoens et al., Tumour ischaemia by interferon-y resembles physiological blood vessel regression, Nature 545 (2017) 98.
P.R. Kunk et al., From bench to bedside a comprehensive review of pancreatic cancer immunotherapy, Journal for immunotherapy of cancer 4 (2016) 14.
Y. Zhao et al., Can nanomedicines kill cancer stem cells?, Adv. Drug Delivery. Rev. 65 (2013) 1763-1783.
J. Sun et al., Programmable co-delivery of the immune checkpoint inhibitor NLG919 and chemotherapeutic doxorubicin via a redox-responsive immunostimulatory polymeric prodrug carrier, Acta Pharmacol. Sin. 38 (2017) 823-834.
G.M. Soliman et al., Dendrimers and miktoarm polymers based multivalent nanocarriers for efficient and targeted drug delivery, Chem. Commun. 47 (2011) 9572-9587.
Y. Jiang et al., The interplay of size and surface functionality on the cellular uptake of sub-10 nm gold nanoparticles, ACS Nano 9 (2015) 9986-9993.
J. Wang et al., The role of micelle size in tumor accumulation, penetration, and treatment, ACS Nano 9 (2015) 7195-7206.
R. Nagarajan et al., Block copolymer self?assembly in selective solvents: Spherical micelles with segregated cores, The Journal of Chemical Physics 90 (1989) 5843-5856.
K. Mortensen et al., Poly (ethylene oxide)-poly (propylene oxide)-poly (ethylene oxide) triblock copolymers in aqueous solution. The influence of relative block size, Macromolecules 26 (1993) 4128-4135.
Y.H. Bae et al., Stability issues of polymeric micelles, J. Control. Release 131 (2008) 2-4.
H. Chen et al., Fast release of lipophilic agents from circulating PEG-PDLLA micelles revealed by in vivo forster resonance energy transfer imaging, Langmuir 24 (2008) 5213-5217.
A. Schulz et al., Drug-induced morphology switch in drug delivery systems based on poly (2-oxazoline) s, ACS Nano 8 (2014) 2686-2696.
A. Reisch et al., Charge-controlled nanoprecipitation as a modular approach to ultrasmall polymer nanocarriers: making bright and stable nanoparticles, ACS Nano 9 (2015) 5104-5116.
Y. Wang et al., Dissipative particle dynamics simulation study on the mechanisms of self-assembly of large multimolecular micelles from amphiphilic dendritic multiarm copolymers, Soft Matter 9 (2013) 3293-3304.
Qiu, J.; et al., Controlled/living radical polymerization in aqueous media: homogeneous and heterogeneous systems, Prog. Polym. Sci. 2001, 26, 2083-2134.
Matyjaszewski, K., Davis, T. P., Statistical, Gradient, Block, and Graft Copolymers by Controlled/Living Radical Polymerizations; Advances in Polymer Science; vol. 159; 2002, 1-168.
Matyjaszewski, K., Controlled Radical Polymerization; ACS: Washington, D. C., 1998 ACS Symposium Series 685.
Matyjaszewski, K., Controlled/Living Radical Polymerization. Progress in ATRP, NMP, and RAFT; ACS: Washington, D. C., 2000; ACS Symposium Series 768.
Matyjaszewski, K., Davis, T. P., Handbook of Radical Polymerization; Wiley: Hoboken, 2002, 1-923.
Lu. J. eL al., PEG_derivatized embelin as a nanomicellar carrier for delivery of paclitaxel to breast and prostate cancers, Biomaterials, Nov. 23, 2012 (E-pub), vol. 34, 1591-1600.
Xiao, K et al., A self-assembling nanoparticle for paclitaxel delivery in ovarian cencer, Biomaterials, 2009, vol. 30, 6006-6016.
Tian, Lu et al., Core Crosslinkable Polymeric Micelles from PEG-Lipid Amphiphiles as Drug Carriers, J. Matter. Chem., 2004, 14, 2317-2324.
Bhadra D. et al., Pegylated Lysine Based Copolymeric Dendritic Micelles for Solubilization Ans Delivery Of Artemether, Journal of Pharmacy and Pharmaceutical Sciences, Canadian Society for Pharmaceutical Sciences, Edmonton, CA, vol. 8. No. 3, Sep. 2, 2005, pp. 467-482.
Sang Cheon Lee et al, Hydrotropic Polymeric Micelles for Enhanced Paclitaxel Solubility: In Vitro and In Vivo Characterization, Biomacromolecules, vol. 8. No. 1, Dec. 1, 2006, pp. 202-208.
Saravanakumar G et al., Hydrotropic hyaluronic acid conjugates: Synthesis, characterization and implications as a carrier of paclitaxel, International Journal of Pharmaceutics, Elsevier BV, NL, vol. 394. No. 1-2, Jul. 15, 2010, pp. 154-161.
Saravanakumar G et al., Hydrotropic oligomer-conjugated glycol chitosan as a carrier of paclitaxel: Synthesis characterization and in vivo biodistribution, Journal of Controlled Release, Elsevier, Amsterdam, NL, vol. 140, No. 3, Dec. 16, 2009, pp. 210-217.
Ian W. Hamley et al., A Thermoresponsive Hydrogel Based on Telechelic PEG End-Capped with Hydrophobic Dipeptides, Macromolecular Bioscience, vol. 11, No. 8, May 6, 2011, pp. 1068-1078.
Peng Zhang et al., Design and Evaluation of a PEGylated Lipopeptide Equipped with Drug-Interactive Motifs as an Improved Drug Carrier, The AAPS Journal, vol. 16, No. 1, Nov. 27, 2013, pp. 114-124.
Ischakov Rafael et al., Peptide-based hydrogel nanoparticles as effective drug delivery agents, Bioorganic & Medicinal Chemistry, Pergamon, GB, vol. 21, No. 12, Mar. 21, 2013, pp. 3517-3522.
Xiaolan Zhang et al., PEG-Farnesylthiosalicylate Conjugate as a Nanomicellar Carrier for Delivery of Paclitaxel, Bioconjugate Chemistry, vol. 24, No. 3. Mar. 20, 2013, pp. 464-472.
Jianqin Lu et al., Design and Characterization of PEG-Derivatized Vitamin E as a Nanomicellar Formulation for Delivery of Paclitaxel, Molecular Pharmaceutics, vol. 10, No. 8, Aug. 5, 2013, pp. 2888-2898.
Beg, Sarwar, Bioavailability Enhancement Strategies: Basics, Formulation Approaches and Regulatory Considerations, Current Drug Delivery, 2011, vol. 8, No. 6, pp. 1-12.
Nanjwade, Basavaraj K., Functions of Lipids for Enhancement of Oral Bioavailability of Poorly Water-Soluble Drugs, Sci Pharm. 2011; 79: 705-727.
Buse, Joshua, Properties, engineering and applications of lipid-based nanoparticle drug-delivery systems: current research and advances, Nanomedicine (2010) 5(8), 1237-1260.
Puri, Anu et al., Lipid-Based Nanoparticles as Pharmaceutical Drug Carriers: From Concepts to Clinic, Crit Rev Ther Drug Carrier Syst. 2009 ; 26(6): 523-580.
Narang, Ajit S. et al., Stable drug encapsulation in micelles and microemulsions, International Journal of Pharmaceutics 345 (2007) 9-25.
Jiang, Jianfei et al., A Mitochondria-Targered Nitroxide/Hemigramicisin S Conjugate Protects Mouse Embryonic Cells Against Gamma Irradiation, Int J Radiat Oncol Biol Phys. Mar. 1, 2008; 70(3): 816-825.
Jiang, Jianfei et al., Structural Requirements for Optimized Delivery, Inhibition of Oxidative Stress, and Antiapoptotic Activity of Targeted Nitroxides, The Journal of Pharmacology and Experimental Therapeutics, vol. 320, No. 3, 1050-1060.
Rajagopalan, Malolan S., et al., The Mitochondria-targeted Nitroxide JP4-039 Augments Potentially Lethal Irradiation Damage Repair, in vivo 23: 717-726 (2009).
Epperly, Michael W., et al., Intraesophageal Administration of GS-Nitroxide (JP4-039) Protects Against Ionizing Irradiation-induced Esophagitis, in vivo 24: 811-820 (2010).
Epperly, M., et al., Topical Application of GS-Nitroxide JP4-039 Emulsion Mitigates Ionizing Irradiation Induced Skin Burns, Int. J. Radiation Oncology Biol. Physics. 78(2010)S634-S635.
Goff, Julie P., et al., Radiobiologic Effects of GS-Nitroxide (JP4-039) on the Hematopoietic Syndrome, in vivo 25: 315-324 (2011).
Frantz, Celine-Marie, et al., Large-Scale Asymmetric Synthesis of the Bioprotective Agent JP4-039 and Analogs, Organic Letters (2011), Vo. 13, No. 9, 2318-2321.
Zalipsky, S., et al., Attachment of Drugs to polyethylene Glycols, Eur. Polvm. J. vol. 19, No. 12, pp. 1177 1183, 1983.
Patist, A. et al., On the Measurement of Critical Micelle Concentrations of Pure and Technical-Grade Nonionic Surfactants, Journal of Surfactants and Detergents, vol. 3, No. 1 (Jan. 2000), 53-58.

(56) References Cited

OTHER PUBLICATIONS

Kenworthy, A. K. et al., Range and Magnitude of the Steric Pressure Between Bilayers Containing Phospholipids with Covalently Attached Poly(ethylene glycol), Biophysical Journal vol. 68 May 1995 1921-1936.
Zhu, Peizhi et al., Fluorescence Quenching by Tempo: A Sub-30 A Single-Molecule Ruler, Biophys. J. 89(2005) L37-L39.
Lee, Jaehwi, et al., Hydrotropic Solubilization of Paclitaxel: Analysis of Chemical Structures for Hydrotropic Property, Pharmaceutical Research, vol. 20, No. 7, Jul. 2003, 1022-1030.
Kim, Ji Young, et al., Hydrotropic polymer micelles as versatile vehicles for delivery of poorly water-soluble drugs, Journal of Controlled Release 152 (2011) 13-20.
Dabholkar, Rupa D., et al., Polyethylene glycol-phosphatidylethanolamine conjugate (PEG-PE)-based mixed micelles: Some properties, loading with paclitaxel, and modulation of P-glycoprotein-mediated efflux, International Journal of Pharmaceutics 315 (2006) 148-157.
Luo, Juntao et al., Well-Defined, Size-Tunable, Multifunctional Micelles for Efficient Paclitaxel Delivery for Cancer Treatment, Bioconjugate Chem. 2010, 21, 1216-1224.
Yen, Chiao-Ting, et al., Design and synthesis of new N-(fluorenyl-9-methoxycarbonyl) (Fmoc)-dipeptides as anti-inflammatory agents, European Journal of Medicinal Chemistry 44 (2009) 1933-1940.
Zhang, Yan, et al., Supramolecular Hydrogels Respond to Ligand-Receptor Interaction, J. Am. Chem. Soc. 2003, 125, 13680-13681.
Jayawarna, Vineetha et al., Nanostructured Hydrogels for Three-Dimensional Cell Culture Through Self-Assembly of Fluorenylmethoxycarbonyl-Dipeptides, Adv. Mater. 2006, 18, 611-614.
Mahler, Assaf et al., Rigid, Self-Assembled Hydrogel Composed of a Modified Aromatic Dipeptide, Adv. Mater. 2006, 18, 1365-1370.
Dong, He et al., Long-Circulationg 15nm Micelles Based on Amphiphilic 3-Helix Peptide-PEG Conjugates, ACSNano, vol. 6, No. 6, 5320-5329.
Lukyanov, Anatoly N., et al. Micelles from Lipid Derivatives of Water-Soluble Polymers as Delivery Systems for Poorly Soluble Drugs, Advanced Drug Delivery Reviews, vol. 56, 1273-1289.
Braunecker, Wade et al., Controlled/Living Radical Polymerization: Features, Development, and Perspectives; Prog. Polym. Sci., 2007, 32, 93-146.
Hou Dy, et al. Inhibition of indoleamine 2,3-dioxygenase in dendritic cells by stereoisomers of 1-methyl-tryptophan correlates with anti-tumor responses. Cancer research 67, 792-801 (2007).
Liu X, et al. Selective inhibition of IDO1 effectively regulates mediators of antitumor immunity. Blood 115, 3520-3530 (2010).
Handke N, et al. Elaboration of glycopolymer-functionalized micelles from an N-vinylpyrrolidone/lactide-based reactive copolymer platform. Macromolecular bioscience 13, 1213-1220 (2013).
Broz M L, et al. Dissecting the tumor myeloid compartment reveals rare activating antigen-presenting cells critical for T cell immunity. Cancer Cell, 26, 638-652 (2014).
Matyjaszewski, K. et al., Atom Transfer Radical Polymerization; Chem. Rev. 2001, 101, 2921-2990.
Tsarenskt, N. et al., "Green" Atom Transfer Radical Polymerization: From Process Design to Preparation of Well-Defined Environmentally Friendly Polymeric Materials; Chem Rev 2007, 107, 2270-2299.
Dwanisa Latere, J. P. et al., Prediction of drug solubility in amphiphilic di-block copolymer micelles:the role of polymer-drug compatibility, Pharmazie, 62 (2007) 7, 499-504.
Bae, Younsoo, et al., Intelligent polymeric micelles from functional poly(ethylene glycol)-poly(amino acid) block copolymers, Advanced Drug Delivery Reviews 61 (2009) 768-784.
Kubowicz, Stephan et al., Multicompartment Micelles Formed by Self-Assembly of Linear ABC Triblock Copolymets in Aqueous Medium, Angew.Chem. Int. Ed, 2005, 44, 5262-52-65.
Avasanifar, Alsaneh et al, Poly(ethylene oxide)-block-poly(L-amino acid) micelles for drug deliver, Advanced Drug Delivery Reviews 54 (2002) 169 190.

Mahmud, Abdullah et al., Novel Self-Associating Poly(ethylene oxide)-block-poly(e-caprolactone) Block Copolymers with Functional Side Groups on the Polyester Block for Drug Delivery, Macronolecules 2006, 39, 9119-9428.
Mathias, Errol V., et al., Model of Drug-Loaded Fluorocarbon-Based Micelles Studied by Electron-Spin Indiced F Relaxation NMR and Molecular Dynamics Simulation, Langmuir, 2008, 24, 692-700.
Mor, Adam et al., Inhibition of Contact Sensitivity by Farnesylthiosalicylic Acid-Amide, a Potentional Rap1 Inhibitor, Journal of Investigative Dermatology (2011), vol. 131, 2040-2048.
Ryan, Derek M. et al., Complementary pi-pi Interactions Induce Multicomponent Coassembly into Functionsl Fibrils, Langmuir 2011, 27, 11145-11156.
Slaughter, Jennifer N., et al. Synthesis and sel-assembly properties of a novel [poly(ethylene glycol)]-fluorocarbon-phospholipid triblock copolimer, Tetrahedron Letters, 48 (2007) 3879-3882.
M. Ogawa et al., Sensitivity to gemcitabine and its metabolizing enzymes in neuroblastoma, Clin. Cancer Res. 11 (2005) 3485-3493.
J.L. Abbruzzese et al., A phase I clinical, plasma, and cellular pharmacology study of gemcitabine, J. Clin. Oncol. 9 (1991) 491-498.
J. Kleeff et al., Pancreatic cancer microenvironment, Int. J. Cancer 121 (2007) 699-705.
S. Lunardi et al., The stromal compartments in pancreatic cancer: are there any therapeutic targets?, Cancer Lett. 343 (2014) 147-155.
US National Library of Medicine. ClinicalTrials.gov [online], https://clinicaltrials.gov/ct2/show/NCT02077881.Mar. 4, 2014.
Shevchenko et al., Low-dose gemcitabine depletes regulatory T cells and improves survival in the orthotopic Panc02 model of pancreatic cancer, Int. J. Cancer 133 (2013) 98-107.
L. Partecke et al., A syngeneic orthotopic murine model of pancreatic adenocarcinoma in the C57/BL6 mouse using the Panc02 and 6606PDA cell lines, Eur. Surg. Res. 47 (2011) 98-107.
B.-F. Pan et al., Mechanisms of resistance to 6-thioguanine in a murine pancreatic tumor, Cancer Chemother. Pharmacol. 29 (1992) 471-474.
J. Sun et al., Intracellular plasmid DNA delivery by self-assembled nanoparticles of amphiphilic PHML-b-PLLA-b-PHML copolymers and the endocytosis pathway analysis, J. Biomater. Appl. 31 (2016) 606-621.
P.E. Saw et al., Hyper-cell-permeable micelles as a drug delivery carrier for effective cancer therapy, Biomaterials 123 (2017) 118-126.
Zhang, X., et al. Tunable pH-Responsive Polymeric Micelle for Cancer Treatment. ACS Macro Letters 4, 620-623 (2015).
Gao, X. et al. Nanoassembly of surfactants with interfacial drug-interactive motifs as tailor-designed drug carriers, Molecular Pharmaceutics, Dec. 17, 2012 (E-pub) vol. 10, pp. 187-198.
Y.X. Huang, J.Q. Lu, X. Gao, J. Li, W.C. Zhao, M. Sun, D.B. Stolz, R. Venkataramanan, L.C. Rohan,S. Li, PEG-Derivatized Embelin as a Dual Functional Carrier for the Delivery of Paclitaxel, Bioconjugate Chem, 23 (2012) 1443-1451.
Chen, Y., et al. Targeted delivery of curcumin to tumors via PEG-derivatized FTS-based micellar system. The AAPS Journal 16, 600-608 (2014).
Zhang, X., et al. PEG-famesyl thiosalicylic acid telodendrimer micelles as an improved formulation for targeted delivery of paclitaxel. Molecular pharmaceutics 11, 2807-2814 (2014).
Zhang, X., et al. Reduction-sensitive dual functional nanomicelles for improved delivery of paclitaxel. Bioconjugate chemistry 25, 1689-1696 (2014).
Zhang, P., et al. A PEG-Fmoc conjugate as a nanocarrier for paclitaxel. Biomaterials 35, 7146-7156 (2014).
Zhang, X., et al. Targeted delivery of anticancer agents via a dual function nanocarrier with an interfacial drug-interactive motif. Biomacromolecules 15, 4326-4335 (2014).
M.M. Yallapu, M. Jaggi, S.C. Chauhan, Curcumin nanoformulations: a future nanomedicine for cancer, Drug discovery today, 17 (2012) 71-80.
L. Liu, L. Sun, Q.J. Wu, W.H. Guo, L. Li, Y.S. Chen, Y.C. Li, C.Y. Gong, Z.Y. Qian, Y.Q. Wei, Curcumin loaded polymeric micelles

(56) References Cited

OTHER PUBLICATIONS inhibit breast tumor growth and spontaneous pulmonary metastasis, Int J Pharmaceut, 443 (2013) 175-182.
Wolfson, E., et al. Enhancing FTS (Salirasib) efficiency via combinatorial treatment. Biology of the cell 107, 130-143 (2015).
Zhang, X., et al. PEG-farnesylthiosalicylate conjugate as a nanomicellar carrier for delivery of paclitaxel. Bioconjugate Chem. 24, 464-472 (2013).
L. Li, F.S. Braiteh, R. Kurzrock, Liposome-encapsulated curcumin: in vitro and in vivo effects on proliferation, apoptosis, signaling, and angiogenesis, Cancer, 104 (2005) 1322-1331.
Marciano, D. et al., Farnesyl derivatives of rigid carboxylic acids-inhibitors of ras-dependent cell growth. J. Med. Chem. 38, 1267-72 (1995).
Xiong, X. B. et al., Enhanced intracellular delivery and improved antitumor efficacy of doxorubicin by sterically stabilized liposomes modified with a synthetic RGD mimetic. J. Control. Release, 107, 262-75 (2005).
Lu, J. et al. PEG-derivatized embelin as a nanomicellar carrier for delivery of paclitaxel to breast and prostate cancers. Biomaterials, 34, 1591-1600 (2013).
Xiao, K. et al. A self-assembling nanoparticle for paclitaxel delivery in ovarian cancer, Biomaterials, 2009. vol. 30, pp. 6006-6016.
H. Maeda, J. Wu, T. Sawa, Y. Matsumura, K. Hori, Tumor vascular permeability and the EPR effect in macromolecular therapeutics: a review, J Control Release, 65 (2000) 271-284.
A.B. Kunnumakkara, P. Anand, B.B. Aggarwal, Curcumin inhibits proliferation, invasion, angiogenesis and metastasis of different cancers through interaction with multiple cell signaling proteins, Cancer letters, 269 (2008) 199-225.
L.R. Chaudhary, K.A. Hruska, Inhibition of cell survival signal protein kinase B/Akt by curcumin in human prostate cancer cells, J Cell Biochem, 89 (2003) 1-5.
S. Lev-Ari, L. Strier, D. Kazanov, L. Madar-Shapiro, H. Dvory-Sobol, I. Pinchuk, B. Marian, D. Lichtenberg, N. Arber, Celecoxib and curcumin synergistically inhibit the growth of colorectal cancer cells, Clinical cancer research : an official journal of the American Association for Cancer Research, 11 (2005) 6738-6744.
M. Notarbartolo, P. Poma, D. Perri, L. Dusonchet, M. Cervello, N. D'Alessandro, Antitumor effects of curcumin, alone or in combination with cisplatin or doxorubicin, on human hepatic cancer cells. Analysis of their possible relationship to changes in NF-KB activation levels and in IAP gene expression, Cancer letters, 224 (2005) 53-65.
B. Rotblat, M. Ehrlich, R. Haklai, Y. Kloog, The Ras inhibitor farnesylthiosalicylic acid (Salirasib) disrupts the spatiotemporal localization of active Ras: A potential treatment for cancer, Method Enzymol, 439 (2008) 467-489.
M. Marom, R. Haklai, G. Benbaruch, D. Marciano, Y. Egozi, Y. Kloog, Selective-Inhibition of Ras-Dependent Cell-Growth by Farnesylthiosalicylic Acid, Journal of Biological Chemistry, 270 (1995) 22263-22270.
Y. Kloog, A.D. Cox, Ras inhibitors: potential for cancer therapeutics, Molecular medicine today, 6 (2000) 398-402.
R. Blum, Y. Kloog, Tailoring Ras-pathway—inhibitor combinations for cancer therapy, Drug resistance updates : reviews and commentaries in antimicrobial and anticancer chemotherapy, 8 (2005) 369-380.
J. Min, A. Zaslavsky, G. Fedele, S.K. Mclaughlin, E.E. Reczek, T. De Raedt, I. Guney, D.E. Strochlic, L.E. Macconaill, R. Beroukhim, R.T. Bronson, S. Ryeom, W.C. Hahn, M. Loda, K. Cichowski, An oncogene-tumor suppressor cascade drives metastatic prostate cancer by coordinately activating Ras and nuclear factor-kappaB, Nature medicine, 16 (2010) 286-294.
M. Gana-Weisz, J. Halaschek-Wiener, B. Jansen, G. Elad, R. Haklai, Y. Kloog, The Ras inhibitor S-trans, trans-farnesylthiosalicylic acid chemosensitizes human tumor cells without causing resistance, Clinical Cancer Research, 8 (2002) 555-565.
Y. Kloog, A.D. Cox, M. Sinensky, Concepts in Ras-directed therapy, Expert opinion on investigational drugs, 8 (1999) 2121-2140.
R. Haklai, G. Elad-Sfadia, Y. Egozi, Y. Kloog, Orally administered FTS (salirasib) inhibits human pancreatic tumor growth in nude mice, Cancer chemotherapy and pharmacology, 61 (2008) 89-96.
A. Biran, M. Brownstein, R. Haklai, Y. Kloog, Down regulation of survivin and aurora A by histone deacetylase and RAS inhibitors: a new drug combination for cancer therapy, International journal of cancer. Journal International du cancer, 128 (2011) 691-701.
L. Mologni, S. Brussolo, M. Ceccon, C. Gambacorti-Passerini, Synergistic effects of combined Wnt/KRAS inhibition in colorectal cancer cells, PloS one, 7 (2012) e51449.
P. Anand, A.B. Kunnumakkara, R.A. Newman, B.B. Aggarwal, Bioavailability of curcumin: problems and promises, Molecular pharmaceutics, 4 (2007) 807-818.
A. Kraitzer, Y. Kloog, R. Haklai, M. Zilberman, Composite fiber structures with antiproliferative agents exhibit advantageous drug delivery and cell growth inhibition in vitro, Journal of pharmaceutical sciences, 100 (2011) 133-149.
H. Cabral, Y. Matsumoto, K. Mizuno, Q. Chen, M. Murakami, M. Kimura, Y. Terada, M.R. Kano, K. Miyazono, M. Uesaka, N. Nishiyama, K. Kataoka, Accumulation of sub-100 nm polymeric micelles in poorly permeable tumours depends on size, Nat Nanotechnol, 6 (2011) 815-823.
X. Gao, L. Huang, Potentiation of cationic liposome-mediated gene delivery by polycations, Biochemistry, 35 (1996) 1027-1036.
C. Ramachandran, H.B. Fonseca, P. Jhabvala, E.A. Escalon, S.J. Melnick, Curcumin inhibits telomerase activity through human telomerase reverse transcritpase in MCF-7 breast cancer cell line, Cancer letters, 184 (2002) 1-6.
R.A. McPherson, M.C. Conaway, C.W. Gregory, W. Yue, R.J. Santen, The novel ras antagonist, farnesylthiosalicylate, suppresses growth of prostate cancer in vitro, Prostate, 58 (2004) 325-334.
P. Starkel, N. Charette, I. Borbath, T. Schneider-Merck, C. De Saeger, J. Abarca, I. Leclercq, Y. Horsmans, Ras inhibition in hepatocarcinoma by S-trans-trans-farnesylthiosalicyclic acid: association of its tumor preventive effect with cell proliferation, cell cycle events, and angiogenesis, Molecular carcinogenesis, 51 (2012) 816-825.
K.S. Smalley, T.G. Eisen, Farnesyl thiosalicylic acid inhibits the growth of melanoma cells through a combination of cytostatic and pro-apoptotic effects, International journal of cancer. Journal international du cancer, 98 (2002) 514-522.
H. Aoki, Y. Takada, S. Kondo, R. Sawaya, B.B. Aggarwal, Y. Kondo, Evidence that curcumin suppresses the growth of malignant gliomas in vitro and in vivo through induction of autophagy: role of Akt and extracellular signal-regulated kinase signaling pathways, Molecular pharmacology, 72 (2007) 29-39.
Dong, A et al. Chemical Insights into Antibacterial N-Halamines. Chemical Reviews. vol. 117, Mar. 2, 2017, pp. 4806-4862.
Nakabayashi, Ket al. Recent progress in controlled radical polymerization of N-vinyl Monomers. European Polymer Journal, vol. 49, Jul. 24, 2013, pp. 2808-2838.
Matsuo, Y et al. Precise Synthesis of Block Polymers Composed of Three or More Blocks by Specially Designed Linking Methodologies in Conjunction with Living Anionic Polymerization System. Polymers, vol. 5, Jul. 17, 2013, pp. 1012-1040.
Shipley, L.A. et al., Metabolism and disposition of gemcitabine, and oncolytic deoxycytidine analog, in mice, rats, and dogs, Drug Metabolism and Disposition Nov. 1992, 20 (6) 849-855.
Frese, Kristopher K., et al., nab-Paclitaxel Potentiates Gemcitabine Activity by Reducing Cytidine Deaminase Levels in a Mouse Model of Pancreatic Cancer, Cancer Discovery, Feb. 28, 201-270.
Awasthi, Niranjan et al., Comparative benefits of Nab-paclitaxel over gemcitabine or polysorbate-based docetaxel in experimental pancreatic cancer, Carcinogenesis vol. 34 No. 10 pp. 2361-2369, 2013.
Meng, Huan et al., Use of a Lipid-Coated Mesoporous Silica Nanoparticle Platform for Synergistic Gemcitabine and Paclitaxel Delivery to Human Pancreatic Cancer in Mice, ACSNano, vol. 9, No. 4, pp. 3540-3557, 2015.
Zitvogel, Laurence et al., Immunological aspects of cancer chemotherapy, Nature Reviews, Immunology, vol. 8, Jan. 2008, 59-73.

(56) References Cited

OTHER PUBLICATIONS

Apetoh, Lionel et al., Toll-like receptor 4-dependent contribution of the immune system to anticancer chemotherapy and radiotherapy, Nature Medicine, vol. 13, No. 9, Sep. 2007, pp. 1050-.
Sasso, Maria Stella et al., Low dose gemcitabine-loaded lipid nanocapsules target monocytic myeloid-derived suppressor cells and potentiate cancer immunotherapy, Biomaterials 96 (2016) 47-62.
Uyttenhove, Catherine et al.,Evidence for a tumoral immune resistance mechanism based on tryptophan degradation by indoleamine 2,3-dioxygenase, Nature Medicine, vol. 9, No. 10, Oct. 2003, pp. 1269-1274.
Koblish, Holly K. et al., Hydroxyamidine Inhibitors of Indoleamine-2,3-dioxygenase Potently Suppress Systemic Tryptophan Catabolismand the Growth of IDO-Expressing Tumors, Mol Cancer Ther; 9(2) Feb. 2010, 489-498.
Liu, Xiangdong et al., Selective inhibition of IDO1 effectively regulates mediators of antitumor immunity, Blood, Apr. 2010, vol. 115, No. 17, pp. 3520-3530.
Witkiewicz, Agnes et al., Expression of Indoleamine 2,3-Dioxygenase in Metastatic Pancreatic Ductal Adenocarcinoma Recruits Regulatory T Cells to Avoid Immune Detection, J Am Coll Surg., 2008, pp. 849-854.
Munn, David H et al., Indoleamine 2,3-dioxygenase and tumor-induced tolerance, J Clin Invest. 2007;117(5), 1147-1154.
Nayak, Asha et al., A Phase I study of NLG919 for adult patients with recurrent advanced solid tumors, Journal for ImmunoTherapy of Cancer 2014, 2(Suppl 3), 250-.
Chen, Yichaoet al., An immunostimulatory dual-functional nanocarrier that improves cancer immunochemotherapy, Nature Communications, Nov. 2016, 7:13443, DOI: 10.1038/ncomms13443, www.nature.com/naturecommunications, 1-12.
Danquah, Michael K. et al., Extravasation of polymeric nanomedicines across tumor vasculature, Advanced Drug Delivery Reviews 63 (2011) 623-639.
Chauhan, Vikash P. et al., Strategies for advancing cancer nanomedicine, Nature Materials, vol. 12, Nov. 2013, 958-962.
Cabral, H. et al., Accumulation of sub-100 nm polymeric micelles in poorly permeable tumours depends on size, Nature Nanotechnology, Vo. 6, Decemberpp 2011, 815-823.
Chauhan, Vikash P. et al., Normalization of tumour blood vessels improves the delivery of nanomedicines in a size-dependent manner, Nature Nanotechnology, vol. 7, Jun. 2012, 383-388.
Huang, Keyang et al., Size-Dependent Localization and Penetration of Ultrasmall Gold Nanoparticles in Cancer Cells, Multicellular Spheroids, and Tumors in Vivo, ACSNano, vol. 6, No. 5, 2012, pp. 4483-4493.
Popovic, Zoran et al., A Nanoparticle Size Series for In Vivo Fluorescence Imaging, Angew. Chem. 2010, 122, 8831-8834.
Chauhan, Vikash P. et al., Fluorescent Nanorods and Nanospheres for Real-Time In Vivo Probing of Nanoparticle Shape-Dependent Tumor Penetration, Angew. Chem. 2011, 123, 11619 -11622.
Sun, Jingjing el al., A prodrug micellar carrier assembled from polymers with pendant farnesyl thiosalicylic acid moieties for improved delivery of paclitaxel, Acta Biomaterialia 43 (2016) 282-291.
Bruni, Riccardo et al., Ultrasmall polymeric nanocarriers for drug delivery to podocytes in kidney glomerulus, Journal of Controlled Release 255 (2017) 94-107.
Vandana, Mallaredy et al., Long circulation and cytotoxicity of PEGylated gemcitabine and its potential for the treatment of pancreatic cancer, Biomaterials 31 (2010) 9340-9356.
Chitkara, Deepak et al., Self-Assembling, Amphiphilic Polymer-Gemcitabine Conjugate Shows Enhanced Antitumor Efficacy Against Human Pancreatic Adenocarcinoma, Bioconjugate Chem. 2013, 24, 1161-1173.
Sun, Jingjing el al., Doxorubicin delivered by a redox-responsive dasatinib-containing polymeric prodrug carrier for combination therapy, Journal of Controlled Release 258 (2017) 43-55.
Zauri, Melania et al., CDA directs metabolism of epigenetic nucleosides revealing a therapeutic window in cancer, Nature, vol. 524, Aug. 2015, 114-140.
Weizman, N. et al., Macrophages mediate gemcitabine resistance of pancreatic adenocarcinoma by upregulating cytidine deaminase, Oncogene (2014) 33, 3812-3819.
Kammertoens, Thomas et al., Tumour ischaemia by interferon-γ resembles physiological blood vessel regression, Nature, vol. 545, May 2017, 98-115.
Kunk, Paul R. et al., From bench to bedside a comprehensive review of pancreatic cancer immunotherapy, Journal for ImmunoTherapy of Cancer (2016) 4:14, 1-12.
Zhao, Yi et al., Can nanomedicines kill cancer stem cells?, Advanced Drug Delivery Reviews 65 (2013) 1763-1783.
Sun, Jing-Jing el al.,Programmable co-delivery of the immune checkpoint inhibitor NLG919 and chemotherapeutic doxorubicin via a redox-responsive immunostimulatory polymeric prodrug carrier, Acta Pharmacologica Sinica (2017) 38: 823-834.
Soliman, Ghareb M. et al., Dendrimers and miktoarm polymers based multivalent nanocarriers for efficient and targeted drug delivery, Chem. Commun., 2011, 47, 9572-9587.
Jiang, Ying et al., The Interplay of Size and Surface Functionality on the Cellular Uptake of Sub-10 nm Gold Nanoparticles, ACSNano, vol. 9, No. 10, 2015, 9986-9993.
Wang, Jinqiang et al., The Role of Micelle Size in Tumor Accumulation, Penetration, and Treatment, ACSNano, vol. 9, No. 7, 2015, 7195-7206.
Mortensen, Kell et al., Poly(ethylene oxide)-Poly(propylene oxide)-Poly(ethylene oxide) Triblock Copolymers in Aqueous Solution. The Influence of Relative Block Size, Macromolecules 1993, 26, 4128-4135.
Chen, Hongtao et al., Fast Release of Lipophilic Agents from Circulating PEG-PDLLA Micelles Revealed by in ViWo Forster Resonance Energy Transfer Imaging, Langmuir 2008, 24, 5213-5217.
Schulz, Anita et al., Drug-Induced Morphology Switch in Drug Delivery Systems Based on Poly(2-oxazoline)s, ACSNano, vol. 8, No. 3, 2014, 2686-2696.
Wang, Yulin et al., Dissipative particle dynamics simulation study on the mechanisms of self-assembly of large multimolecular micelles from amphiphilic dendritic multiarm copolymers, Soft Matter, 2013, 9, 3293-3304.
Ogawa, Masahiro et al., Sensitivity to Gemcitabine and Its Metabolizing Enzymes in Neuroblastoma, Clin Cancer Res 2005;11(9), 3485-3493.
Abbruzzese, James L. et al., Phase I Clinical, Plasma, and Cellular Pharmacology Study of Gemcitabine, Journal of Clinical Oncology, vol. 9, No. 3 Mar. 1991: pp. 491-498.
Kleeff, Jorg et al., Pancreatic cancer microenvironment, Int. J. Cancer: 121, 699-705 (2007).
Study of IDO Inhibitor in Combination With Gemcitabine and Nab-Paclitaxel in Patients With Metastatic Pancreatic Cancer, ClinicalTrials.gov Identifier: NCT02077881, 2014, 1-10.
Shevxhenko, Ivan et al., Low-dose gemcitabine depletes regulatory T cells and improves survival in the orthotopic Panc02 model of pancreatic cancer, Int. J. Cancer: 133, 98-107 (2013).
Partecke, L. I. et al., A Syngeneic Orthotopic Murine Model of Pancreatic Adenocarcinoma in the C57/BL6 Mouse Using the Panc02 and 6606PDA Cell Lines, Eur Surg Res 2011;47:98-107.
Pan, Bih-Fang et al., Mechanisms of resistance to 6-thioguanine in a murine pancreatic tumor, Cancer Chemother Pharmacol (1992) 29:471-474.
Sun, Jingjing et al., Intracellular plasmid DNA delivery by self-assembled nanoparticles of amphiphilic PHML-b-PLLA-b-PHML copolymers and the endocytosis pathway analysis, Journal of Biomaterials Applications, 2016, vol. 31 (4) 606-621.
Saw, Phei Er et al., Hyper-cell-permeable micelles as a drug delivery carrier for effective cancer therapy, Biomaterials 123 (2017) 118-126.
Tao Jia., et al., Unimolecular Micelles of Amphiphilic Cyclodextrin-Core Star-Like Copolymers with Covalent pH-Responsive Linkage of Anticancer Prodrugs, Mol. Pharmaceutics, vol. 14, , 2017, pp. 2529-2537.

(56) References Cited

OTHER PUBLICATIONS

Jieni Xu, et al., Pendant HDAC Inhibitor SAHA Derivatized Polymer as a Novel Prodrug Micellar Carrier for Anticancer Drugs, •J. Drug Target (2018), pp. 1-26.

* cited by examiner

Linker L¹ examples:

Linker L² and P examples:
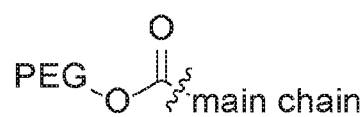
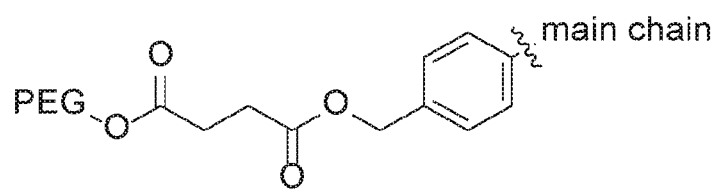
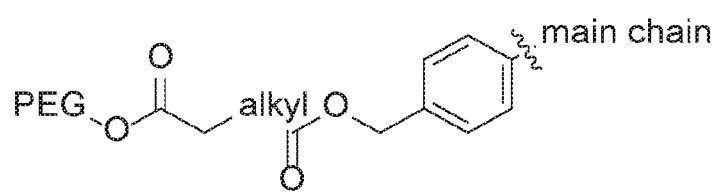
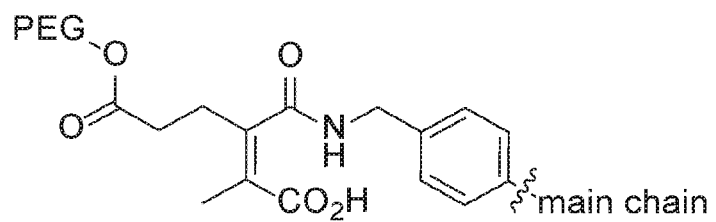
Fig. 5

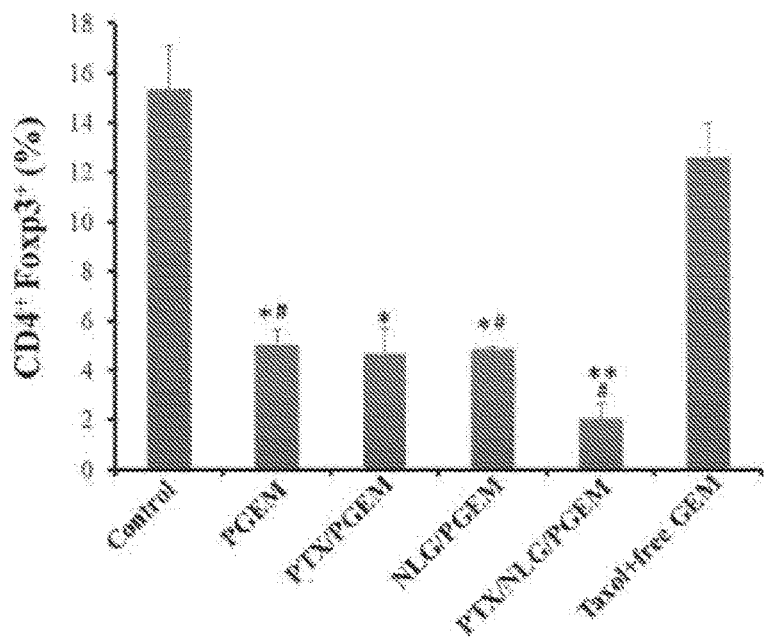
Fig. 12A
Fig. 12B
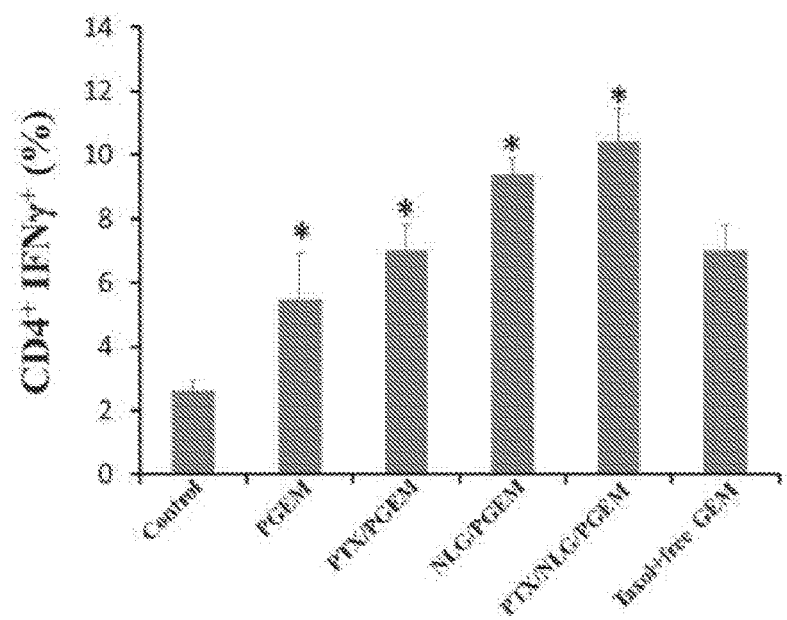
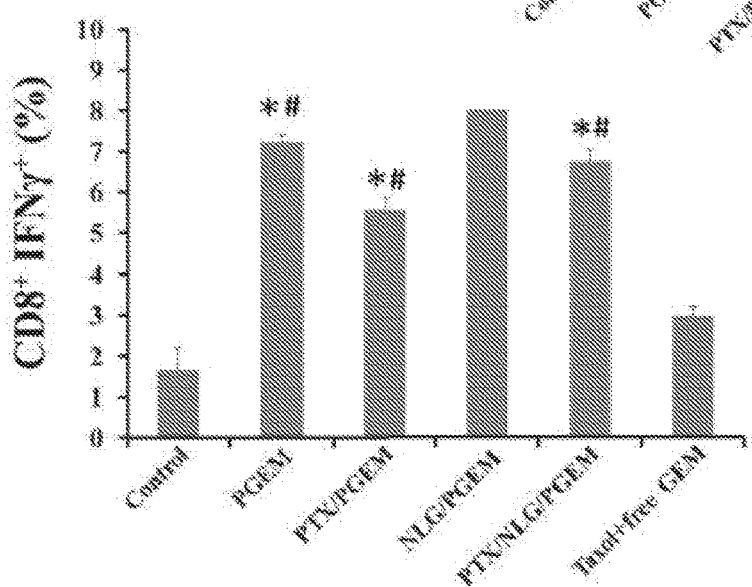
Fig. 12C

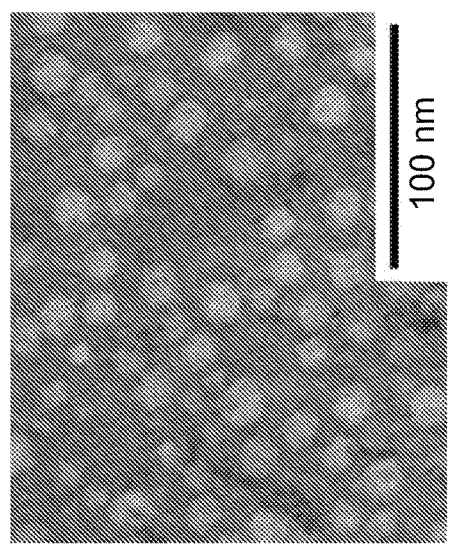
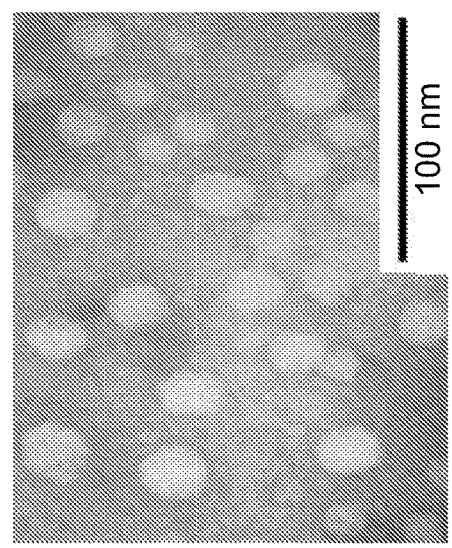
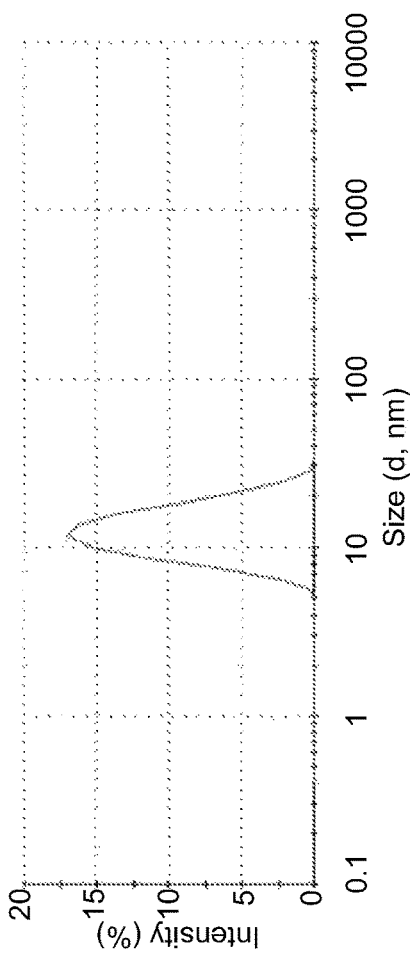
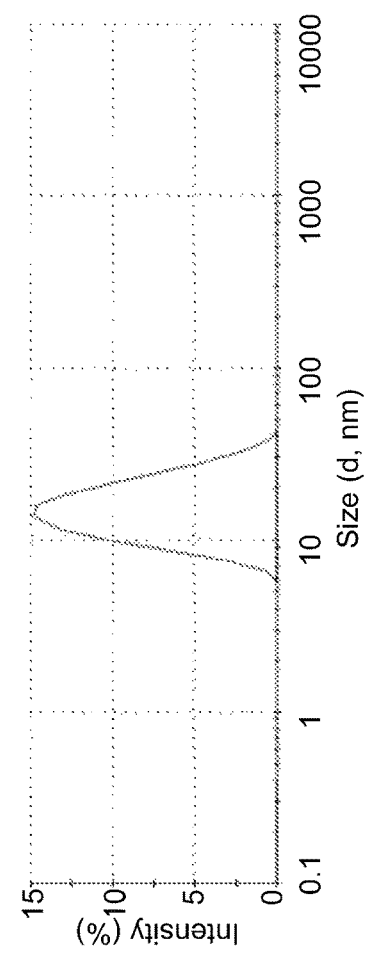
Fig. 14A  Blank micelle size 12.98nm, PDI 0.123
Fig. 14B  DOX-loaded micelle size 16.01nm, PDI 0.114

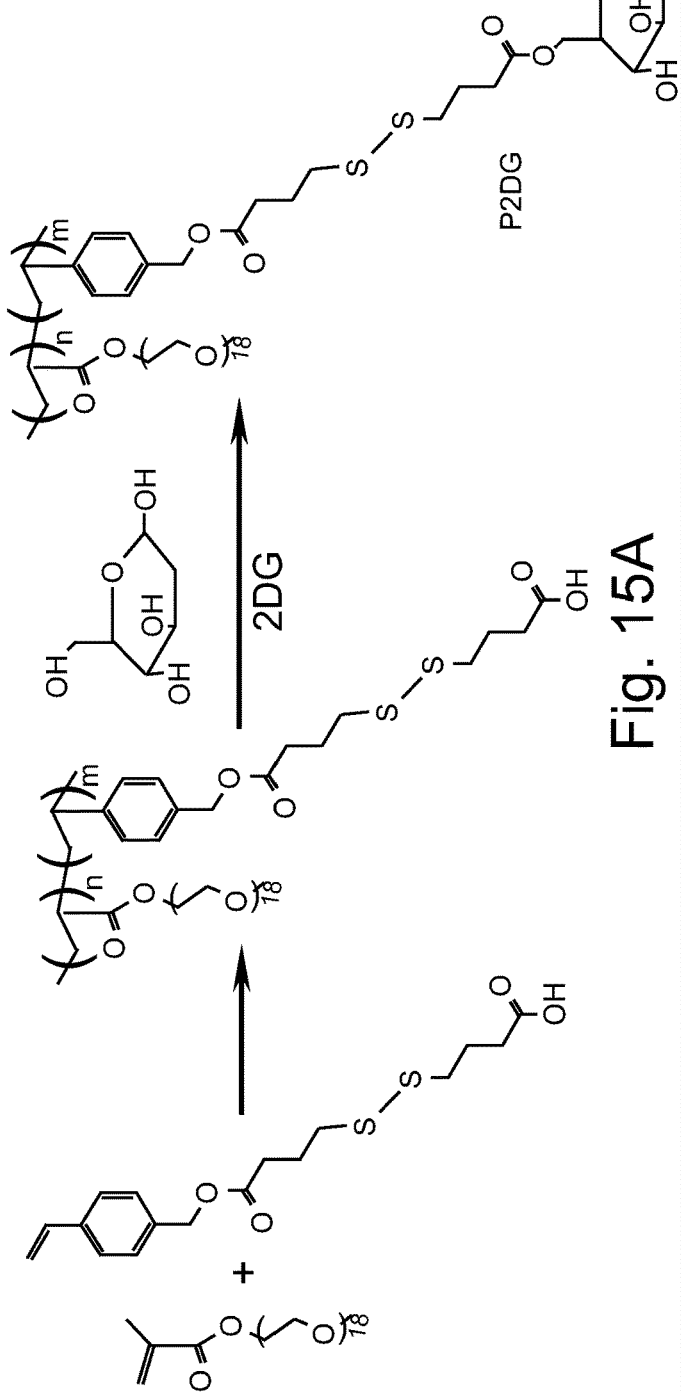
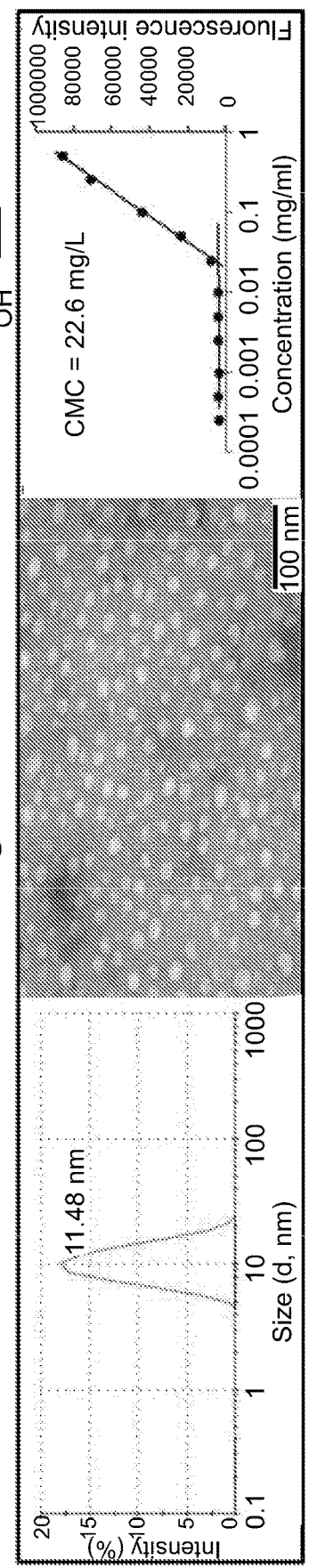
Fig. 15A
Fig. 15B

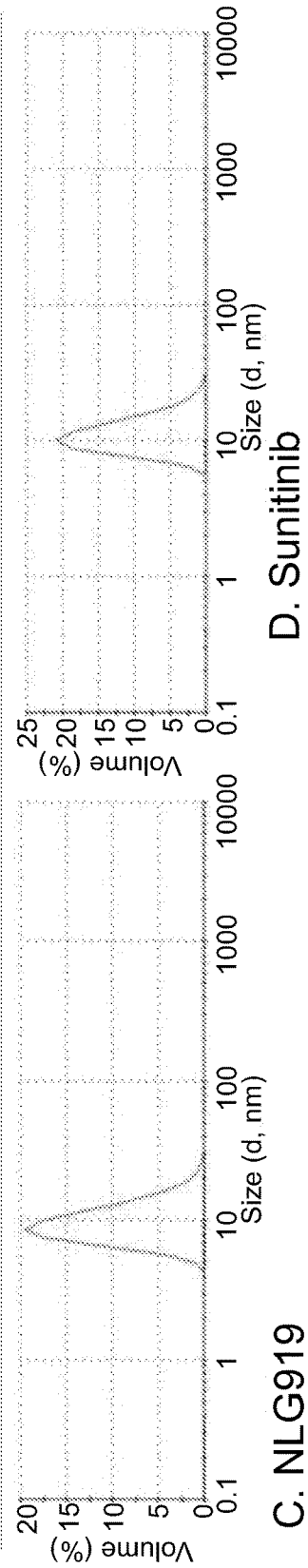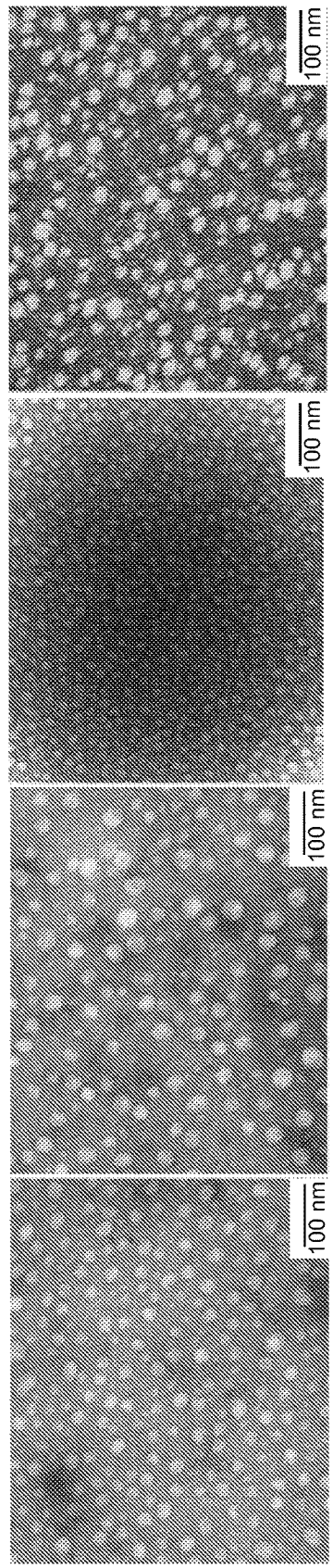
Fig. 16A
A. PTX
B. DOX
C. NLG919
D. Sunitinib
Fig. 16B
PTX/SUN-P2DG
PTX-P2DG
SUN-P2DG
P2DG

SMALL POLYMERIC CARRIERS FOR DELIVERY OF AGENTS

CROSS-REFERENCE TO RELATED APPLICATIONS

This application is a national phase filing of PCT International Patent Application No. PCT/US2019/055766, filed Oct. 11, 2019, which claims benefit of U.S. Provisional Patent Application Ser. No. 62/744,928, filed Oct. 12, 2018, the disclosures of which is are incorporated herein by reference.

GOVERNMENTAL INTEREST

This invention was made with government support under grant number CA174305 and CA223788 awarded by the National Institutes of Health. The government has certain rights in the invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Various small molecules have been developed as potent candidates for therapeutic treatments such as anti-cancer or anti-viral treatment of a patient. However, many drawbacks such as low water solubility, poor bioavailability and high toxic side effects limit clinical applications of such therapeutic agents or compounds. Formulating these drugs into nano-sized micelles can increase the solubility and provide controllable drug delivery, which represents a promising strategy to enhance therapeutic efficacy and reduce systemic toxicity. It is known that the biodistribution profiles and tumor penetration of micelles can be tuned by optimizing the particle size. Decreasing nanoparticle size can increase circulation time and drug accumulation into tumors. However, smaller nanoparticles usually have lower drug payloads and loading efficiencies.

Moreover, it may also be desirable to deliver agents or compounds other than therapeutic agents via nanoparticle carrier agents. Such agents may, for example, have some of the same drawbacks or delivery problems as set forth for therapeutic agents above. For example, it may be desirable to deliver diagnostic agents or compound such as contrast enhancing agents or compound for use in imaging procedures (for example, diagnostic and imaging procedures such as X-ray procedures (including, for example, angiography, venography and urography), computed tomography (CT), magnetic resonance imaging (MRI), ultrasonic imaging, light-based imaging, and positron emission tomography (PET)) either independently of or in combination with other agents or compounds (for example, therapeutic agents).

SUMMARY

In one aspect, a polymer includes a hydrophobic polymer backbone (for example, formed via radical polymerization), a first plurality of pendant groups attached to the hydrophobic polymer backbone and including at least one group including a plurality of hydroxyl groups, and a second plurality of pendant groups attached to the hydrophobic polymer backbone and including at least one hydrophilic polymer.

The at least one of the first plurality of pendant groups and/or the second plurality of pendant groups may, for example, independently be attached to the hydrophobic polymer backbone via a linking moiety. In a number of embodiments, the linking moiety includes at least one group which is interactive via π-π stacking. In a number of embodiments, the first plurality of pendant groups is attached to the hydrophobic polymeric backbone via a first linking group comprising at least a first group which is interactive via π-π stacking. The at least a first group interactive via π-π stacking may, for example, include an aromatic group. The at least a first group interactive via π-π stacking may, for example, include a benzyl group.

In a number of embodiments, the hydrophobic polymer backbone is formed via radical polymerization of vinyl monomers. The hydrophobic polymer backbone may, for example, be formed via a free radical polymerization. The hydrophobic polymer backbone may, for example, be formed via a reversible-deactivation radical polymerization.

In a number of embodiments, the at least one group including a plurality of hydroxyl groups is a hydrophilic group. The at least one group including a plurality of hydroxyl groups may, for example, be adapted to form hydrogen bonds with an aqueous environment. In a number of embodiments, the at least one group including a plurality of hydroxyl groups includes a sugar group. In a number of embodiment, the at least one group including a plurality of hydroxyl groups includes a nucleoside. The at least one group including a plurality of hydroxyl groups may, for example, include a nucleoside analogue, a sugar alcohol, ascorbic acid, 2-Deoxy-D-glucose, triethanolamine, pentaerythritol, tris(hydroxymethyl)aminomethane, dopamine, catechin, or cholic acid. In a number of embodiments, the at least one group including a plurality of hydroxyl groups includes glycerol, di-glycerol, erythritol, xylitol, arabitol, fucitol, ribitol, sorbitol, maltitol, isomalt, mannitol, a saccharide, an oligosaccharides a polysaccharides, ascorbic acid, gluconic acid, glucoronic acid, or glycosamine. In a number of embodiments, the at least one group including a plurality of hydroxyl groups includes glucose, fructose, sucrose, galactose, maltose, trehalose, lactulose, or lactose. In a number of embodiments, the at least one group including a plurality of hydroxyl groups includes ascorbic acid or 2-Deoxy-D-glucose. In a number of embodiments, the nucleoside is ribonucleoside, deoxyribonucleoside, or a nucleoside analogue therapeutic agent. The nucleoside may, for example, be selected from the group consisting of a gemcitabine, azacytidine, cytarabine, or a biologically active derivative thereof. The nucleoside may, for example, be a therapeutic agent.

In a number of embodiments wherein the at least one group including a plurality of hydroxyl groups includes a therapeutic agent or a diagnostic agent, the second plurality of pendant groups is attached to the hydrophobic polymer backbone via a linking moiety that is labile in vivo. The linking moiety that is labile in vivo may, for example, include at least one of a reductive sensitive linkage, a pH-sensitive linkage, a ROS-sensitive linkage, or a protease-sensitive linkage. The linking moiety that is labile in vivo may, for example, include at least one of an ester bond, an orthoester bond, a thioether-ester bond, an anhydride bond, an amid bond, a carbonate bond, a disulfide bond, a hydrazone bond, a cic-acotinyl bond, an acetal bond, a carboxydimethyl maleate bond, an imine bond, an oxime bond, a silyl ether bond, a ketal bond, a thioketal bond or a protease cleavable peptide. As described above, the linking moiety may, for example, further include at least one group which is interactive via π-π stacking. The at least one group interactive via π-π stacking may, for example, include an aromatic group (for example, a benzyl group).

In a number of embodiments, a plurality of the polymers hereof form a micelle having a diameter less than 100 nm, a diameter no greater than 50 nm, a diameter no greater than 30 nm, a diameter no greater than 20 nm. In a number of embodiments, the plurality of the polymers forms a micelle having a diameter in the range of 10 to 30 nm or in the range of 10 to 20 nm.

In another aspect, a formulation hereof may, for example, include a plurality of polymers (as described above) which are formed via radical polymerization to have a hydrophobic polymer backbone, a first plurality of pendant groups attached to the hydrophobic polymer backbone and including at least one group including a plurality of hydroxyl groups and a second plurality of pendant groups attached to the hydrophobic polymer backbone and including at least one hydrophilic polymer. The formulation may further include at least a first compound. The formulation may further include at least a second compound, different from the first compound. The first compound and the second compound may, for example, independently be a first hydrophobic compound and a second hydrophobic compound. One or both of the first compound and the second compound may, for example, independently be a small molecule compound. Such small molecule therapeutic compounds may, for example, have a molecular weight below 1.5 kDa or below 1.0 kDa.

The first compound and/or the second compound may, for example, independently be a therapeutic compound or a diagnostic compound. The first diagnostic compound may, for example, includes a contrast enhancing agent for use in an imaging procedure.

In a number of embodiments, the first compound is a first therapeutic compound such as a chemotherapeutic compound, an antiviral compound (for use, for example, in the treatment of HIV and/or other viral infections), an antibiotic compound, an antimycotic compound, an anticancer compound, an anti-rejection compound, an analgesic compound, an antioxidant compound, an immunomodulating compound, or an anti-inflammatory compound. The first therapeutic compound may, for example, be JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl)oxymethyl-5-isopropylisoxazole), rose bengal, epigallocatechin gallate, simvastatin, curcumin, indomethacin, JQ1, I-BET 151, I-BET 762, resiquimod, riluzole, tamoxifen. NLG-919 (an indoleamine 2,3-dioxygenase (IDO) pathway inhibitor), sunitinib, imatinib, erlotinib, gefitinib, cetuximab, a c-Myc inhibitor such as 10058-F4 (5-[(4-ethylphenyl)methylene]-2-thioxo-4-thiazolidinone), cladribine, fludarabine, nelarabine, troxacitabine, capecitabine, 2'-fluoro-2'-deoxyadenosine, acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, or 9-deazaadenosine. Acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, and 9-deazaadenosine may, for example, be used as antiviral agents.

In a number of embodiments, the second therapeutic compound is independently JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl)oxymethyl-5-isopropylisoxazole), rose bengal, epigallocatechin gallate, simvastatin, curcumin, indomethacin, JQ1, I-BET 151, I-BET 762, resiquimod, riluzole, tamoxifen. NLG-919 (an indoleamine 2,3-dioxygenase (IDO) pathway inhibitor), sunitinib, imatinib, erlotinib, gefitinib, cetuximab, a c-Myc inhibitor such as 10058-F4 (5-[(4-ethylphenyl)methylene]-2-thioxo-4-thiazolidinone), cladribine, fludarabine, nelarabine, troxacitabine, capecitabine, 2'-fluoro-2'-deoxyadenosine, acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, or 9-deazaadenosine As described above, the at least one of the first plurality of pendant groups and/or the second plurality of pendant groups may, for example, independently be attached to the hydrophobic polymer backbone via a linking moiety. In a number of embodiments, the linking moiety includes at least one group which is interactive via π-π stacking. In a number of embodiments, the first plurality of pendant groups is attached to the hydrophobic polymeric backbone via a first linking group comprising at least a first group which is interactive via π-π stacking. The at least a first group interactive via π-π stacking may, for example, include an aromatic group. The at least a first group interactive via π-π stacking may, for example, include a benzyl group.

In a number of embodiments, the hydrophobic polymer backbone is formed via radical polymerization of vinyl monomers. The hydrophobic polymer backbone may, for example, be formed via a free radical polymerization. The hydrophobic polymer backbone may, for example, be formed via a reversible-deactivation radical polymerization.

In a number of embodiments, the at least one group including a plurality of hydroxyl groups is a hydrophilic group. The at least one group including a plurality of hydroxyl groups may, for example, be adapted to form hydrogen bonds with an aqueous environment. In a number of embodiments, the at least one group including a plurality of hydroxyl groups includes a sugar group. In a number of embodiment, the at least one group including a plurality of hydroxyl groups includes a nucleoside. The at least one group including a plurality of hydroxyl groups may, for example, include a nucleoside analogue, a sugar alcohol, ascorbic acid, 2-Deoxy-D-glucose, triethanolamine, pentaerythritol, tris(hydroxymethyl)aminomethane, dopamine, catechin, or cholic acid. In a number of embodiments, the at least one group including a plurality of hydroxyl groups includes glycerol, di-glycerol, erythritol, xylitol, arabitol, fucitol, ribitol, sorbitol, maltitol, isomalt, mannitol, a saccharide, an oligosaccharides a polysaccharides, ascorbic acid, gluconic acid, glucoronic acid, or glycosamine. In a number of embodiments, the at least one group including a plurality of hydroxyl groups includes glucose, fructose, sucrose, galactose, maltose, trehalose, lactulose, or lactose. In a number of embodiments, the at least one group including a plurality of hydroxyl groups includes ascorbic acid or 2-Deoxy-D-glucose. In a number of embodiments, the nucleoside is ribonucleoside, deoxyribonucleoside, or a nucleoside analogue therapeutic agent. The nucleoside may, for example, be selected from the group consisting of a gemcitabine, azacytidine, cytarabine, or a biologically active derivative thereof. The nucleoside may, for example, be a therapeutic agent.

In a number of embodiments wherein the at least one group including a plurality of hydroxyl groups includes a therapeutic agent or a diagnostic agent, the second plurality of pendant groups is attached to the hydrophobic polymer backbone via a linking moiety that is labile in vivo. The linking moiety that is labile in vivo may, for example, include at least one of a reductive sensitive linkage, a pH-sensitive linkage, a ROS-sensitive linkage, or a protease-sensitive linkage. The linking moiety that is labile in vivo may, for example, include at least one of an ester bond, an orthoester bond, a thioether-ester bond, an anhydride bond, an amid bond, a carbonate bond, a disulfide bond, a hydrazone bond, a cic-acotinyl bond, an acetal bond, a carboxydimethyl maleate bond, an imine bond, an oxime bond, a silyl ether bond, a ketal bond, a thioketal bond or a protease cleavable peptide. As described above, the linking moiety may, for example, further include at least one group which is interactive via $\pi$-$\pi$ stacking. The at least one group interactive via $\pi$-$\pi$ stacking may, for example, include an aromatic group (for example, a benzyl group).

In a number of embodiments, a plurality of the polymers hereof form a micelle having a diameter less than 100 nm, a diameter no greater than 50 nm, a diameter no greater than 30 nm, a diameter no greater than 20 nm. In a number of embodiments, the plurality of the polymers forms a micelle having a diameter in the range of 10 to 30 nm or in the range of 10 to 20 nm. The micelle may, for example, have a loading capacity for the first therapeutic compound of at least 4-30% by weight, at least 8-30% by weight or at least 8-20% by weight.

In another aspect, a formulation for delivery of compounds in vivo hereof includes a plurality of polymers (as described above) including a hydrophobic polymer backbone (which may be formed via radical polymerization), a first plurality of pendant groups attached to the hydrophobic polymer backbone and including at least one group including a plurality of hydroxyl groups, and a second plurality of pendant groups attached to the hydrophobic polymer backbone and including at least one hydrophilic polymer. The formulation may further include at least a first compound. The formulation may further include at least a second compound, different from the first compound. The first compound and the second compound may, for example, independently be a first hydrophobic compound and a second hydrophobic compound. The first compound and/or the second compound may, for example, independently be a therapeutic compound or a diagnostic compound. One or both of the first compound and the second compound may, for example, be a small molecule compound. Such small molecule therapeutic compounds may, for example, have a molecular weight below 1.5 kDa or below 1.0 kDa. The plurality of polymers may, for example, form micelles.

In another aspect, a method of formulating a composition for delivery of a first compound includes mixing a plurality of polymers (as described above) including a hydrophobic polymer backbone (which may be formed via radical polymerization), a first plurality of pendant groups attached to the hydrophobic polymer backbone and including at least one group including a plurality of hydroxyl groups, and a second plurality of pendant groups attached to the hydrophobic polymer backbone and including at least one hydrophilic polymer with a plurality of the first compound. The formulation may further include at least a plurality of a second compound, different from the first compound. As described above, the first compound and the second compound may, for example, independently be a first hydrophobic compound and a second hydrophobic group. The first compound and/or the second compound may, for example, independently be a therapeutic compound or a diagnostic compound. One or both of the first compound and the second compound may, for example, be a small molecule compound. Such small molecule therapeutic compounds may, for example, have a molecular weight below 1.5 kDa or below 1.0 kDa. The plurality of polymers may, for example, form micelles.

In a further aspect, a method of delivering a first compound includes administering a formulation including a plurality of polymers (as described above) including a hydrophobic polymer backbone (which may be formed via radical polymerization), a first plurality of pendant groups attached to the hydrophobic polymer backbone and including at least one group comprising a plurality of hydroxyl groups, and a second plurality of pendant groups attached to the hydrophobic polymer backbone and including at least one hydrophilic polymer, and a plurality of the first compounds. The formulation may further include at least a plurality of a second compound, different from the first compound. The first compound and the second compound may, for example, be a hydrophobic compound. The first compound and/or the second compound may, for example, be a therapeutic compound or a diagnostic compound. The first compound and the second compound may, for example, be a small molecule compound. Such small molecule therapeutic compounds may, for example, have a molecular weight below 1.5 kDa or below 1.0 kDa. In a number of embodiments, the plurality of polymers forms micelles and the first compound and/or second compound may be loaded within the micelles.

The present systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 5 illustrates representative linker groups $L^2$ of FIGS. 1 and 2.

FIG. 12A illustrates flow cytometry analysis of $CD4^+$ $FoxP3^+$ Treg immune cells in tumor tissues after treatment with various formulations wherein the percentage of tumor infiltrating immune cells was correspondingly quantified, and wherein the results are reported as mean S.D;*$p<0.05$, **$p<0.01$ (vs control), #$p<0.05$ (vs Taxol+free GEM).

FIG. 12B illustrates flow cytometry analysis of $CD4^+$ $IFN\gamma^+$ T immune cells in tumor tissues after treatment with various formulations wherein the percentage of tumor infiltrating immune cells was correspondingly quantified, and wherein the results are reported as mean±S.D;*$p<0.05$ (vs control).

FIG. 12C illustrates flow cytometry analysis of $CD8^+$ $IFN\gamma^+$ T immune cells in tumor tissues after treatment with various formulations wherein the percentage of tumor infiltrating immune cells was correspondingly quantified, and wherein the results are reported as mean±S.D;*$p<0.05$, (vs control), #$p<0.05$ (vs Taxol+free GEM).

FIG. 14A illustrates a DLS particle size study and a TEM image of blank PAza micelles.

FIG. 14B illustrates a DLS particle size study and a TEM image of DOX-loaded PGAza micelles.

FIG. 15A illustrates a synthetic scheme for the synthesis of P2DG polymer, wherein 2DG is 2-deoxy-D-glucose.

FIG. 15B illustrates a DLS particle size study of P2DG, a TEM image of blank P2DG micelles and a fluorescine intensity study thereof.

FIG. 16A illustrates DLC particle size studies for P2DG loaded with: PTX (panel A), DOX (panel B), NLG919 (panel C) and sunitinib (SUN; panel D).

FIG. 16B illustrates TEM images of blank P2DG and P2DG loaded with: sunitinib (SUN), PTX and PTX/SUN.

DESCRIPTION

Figure 1:
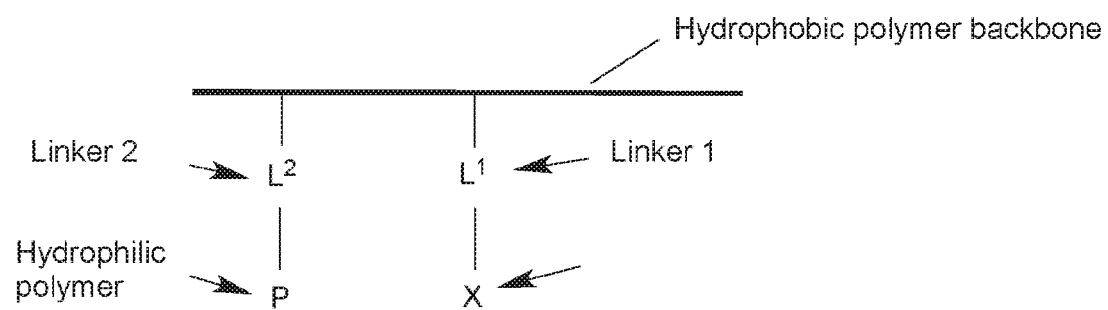
FIG. 1 illustrates schematically a representative embodiment of the generalized structure of an amphiphilic polymers hereof.

The present devices, systems, methods and compositions, along with the attributes and attendant advantages thereof, will best be appreciated and understood in view of the following description taken in conjunction with any accompanying drawings.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a compound" includes a plurality of such compounds and equivalents thereof known to those skilled in the art, and so forth, and reference to "the compound" is a reference to one or more such compounds and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

As used herein, the term "polymer" refers to a chemical compound that is made of a plurality of small molecules or monomers that are arranged in a repeating structure to form a larger molecule. Thus, a polymer is a compound having multiple repeat units (or monomer units) and includes the term "oligomer," which is a polymer that has only a few repeat units. The term "copolymer" refers to a polymer including two or more dissimilar repeat units (including terpolymers—comprising three dissimilar repeat units—etc.). Polymers may occur naturally or be formed synthetically. The use of the term "polymer" encompasses homopolymers as well as copolymers. The term "copolymer" is used herein to include any polymer having two or more different monomers. Copolymers may, for example, include alternating copolymers, periodic copolymers, statistical copolymers, random copolymers, block copolymers, graft copolymers etc. Examples of polymers include, for example, polyalkylene oxides.

As used herein, the term "pendant" refers to a group or moiety attached to a backbone chain of a long molecule such as a polymer as described above. Pendant group may be either (1) short chain or low molecular weight groups or (2) long chain or high molecular groups such as polymers. Pendant groups are sometime referred to as side groups. Long chain pendant groups or high molecular weight pendant groups are sometimes referred to as "pendant chains" or "side chains".

In a number of embodiments, systems, formulations, methods and compositions hereof are provided for co-delivery of small molecule therapeutic agents or drugs (for example, chemotherapeutic, therapeutic agents or drugs) and nucleic acid-based therapeutic agents or drugs simultaneously.

Figure 2:
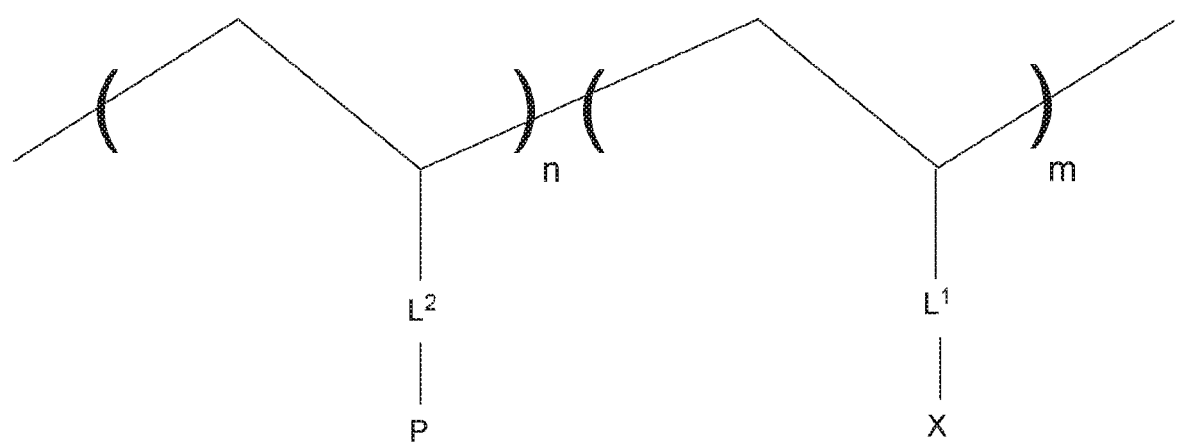
FIG. 2 illustrates schematically another representative embodiment of the generalized structure of an amphiphilic polymer hereof.

FIGS. 1 and 2 illustrated schematically amphiphilic polymers hereof. The amphiphilic polymer may, for example, be formed via radical polymerization to have a hydrophobic polymer backbone. The hydrophobic polymer backbone may, for example, be formed via a free radical polymerization or via a reversible-deactivation radical polymerization or RDRP (formerly referred to as controlled radical polymerization or CRP).

Reversible-Deactivation Radical Polymerization (RDRP) procedures include, for example, Nitroxide Mediated Polymerization (NMP), Atom Transfer Radical Polymerization (ATRP), and Reversible Addition Fragmentation Transfer (RAFT) and others (including cobalt mediated transfer) that have evolved over the last two decades. RDRP provide access to polymer and copolymers comprising radically polymerizable/copolymerizable monomers with predefined molecular weights, compositions, architectures and narrow/controlled molecular weight distributions. Because RDRP processes can provide compositionally homogeneous well-defined polymers, with predicted molecular weight, narrow/designed molecular weight distribution, and high degrees of α- and ω-chain end-functionalization, they have been the subject of much study, as reported in several review articles and ACS symposia. See, for example, Qiu, J.; Charleux, B.; Matyjaszewski, K., *Prog. Polym. Sci.* 2001, 26, 2083; Davis, K. A.; Matyjaszewski, K. *Adv. Polym. Sci.* 2002, 159, 1; Matyjaszewski, K., Ed. Controlled Radical Polymerization; ACS: Washington, D.C., 1998; ACS Symposium Series 685. Matyjaszewski, K., Ed.; Controlled/Living Radical Polymerization. Progress in ATRP, NMP, and RAFT; ACS: Washington, D.C., 2000; ACS Symposium Series 768; and Matyjaszewski, K., Davis, T. P., Eds. Handbook of Radical Polymerization; Wiley: Hoboken, 2002, the disclosures of which are incorporated herein by reference.

The hydrophobic polymer backbone may be formed via radical polymerization of a variety of radically polymerizable monomers. Such monomers may, for example, include pendant groups as described above prior to polymerization. Alternatively, such pendant groups may be attached after polymerization. Representative monomer for use herein include styrene, acrylic acid, methacrylic acid, acrylonitrile, vinyl monomers and their derivatives. In a number of embodiments, the degree of polymerization for hydrophobic polymers hereof is, for example, less than 500, less than 200 or less than 100.

In a number of embodiments, the polymer further includes a first plurality of pendant groups (X) attached to the hydrophobic polymer backbone and including a plurality (that is, at least two) of hydroxyl group (—OH) (that is, polyols) and a second plurality of pendant groups attached to the hydrophobic polymer backbone and including at least one hydrophilic polymer (P). In a number of embodiments, at least one of the first plurality of pendant groups and the second plurality of pendant groups is attached to the hydrophobic polymer backbone via a linking moiety. The linking moiety may include at least one group interactive via π-π stacking. The first plurality of pendant groups may, for example, be attached to the hydrophobic polymeric backbone via a first linking group ($L^1$). The first linking group ($L^1$) may, for example, include at least a first group which is interactive via π-π stacking. The first linking group ($L^1$) may be absent and the group X may be directly attached to the hydrophobic polymer backbone. The second plurality of pendant groups may also be attached to the hydrophobic polymer backbone via a second linking group ($L^2$). The second linking group ($L^2$) may be absent and the hydrophilic polymer may be directly attached to the hydrophobic polymer backbone. The second linking group ($L^2$) may, for example, independently include at least a second group interactive via π-π stacking. The first linking group ($L^1$) and/or the second linking group ($L^2$) may, for example, include an aromatic group. In general, aromatic groups are cyclic molecules including resonance bonds that exhibit increased stability compared to other geometric or connective arrangements with the same set of atoms. Aromatic groups include, for example, benzyl and naphthyl groups. In a number of embodiments hereof, aromatic groups hereof are benzyl groups.

Suitable polyols for use herein include, for example, sugar groups, nucleosides, sugar alcohols, sterols and other groups. In a number of embodiments, representative polyols include a nucleoside, a nucleoside analogue, ascorbic acid, 2-Deoxy-D-glucose, triethanolamine, pentaerythritol, tris (hydroxymethyl)aminomethane, dopamine, catechin, cholic acid, glycerol, di-glycerol, erythritol, xylitol, arabitol, fucitol, ribitol, sorbitol, maltitol, isomalt, mannitol, a saccharide, an oligosaccharides a polysaccharides, ascorbic acid, gluconic acid, glucoronic acid, or glycosamine. Representative saccharides include, for example, glucose, fructose, sucrose, galactose, maltose, trehalose, lactulose, or lactose. In a number of embodiments, a polyol nucleoside hereof is ribonucleoside, deoxyribonucleoside, or a nucleoside analogue therapeutic agent (for example, gemcitabine, azacitidine or cytarabine). In a number of embodiments, the polyol is ascorbic acid or 2-Deoxy-D-glucose.

The hydrophilic oligomer or the hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiments, the at least one hydrophilic polymer is a polyalkylene oxide. The polyalkylene oxide may, for example, be a polyethylene glycol. A polyethylene glycol or other hydrophilic polymer hereof may, for example, have a molecular weight of at least 500 Da. In a number of embodiments, the polyethylene glycol of other hydrophilic polymer hereof has a molecular weight in the range of 100 Da to 5 KDa or in the range of 500 Da to 2 KDa.

Pendant groups hereof such as the first plurality of pendant groups and/or the second plurality of pendant groups may, for example, be attached to the hydrophobic polymer backbone via a linking group including a moiety or bond that is labile. The group or moiety that is labile (in vivo) may, for example, include at least one of a hydrolytically labile group, a reductive sensitive linkage, a pH-sensitive linkage, a ROS-sensitive linkage, or an enzyme/protease-sensitive linkage. The labile linking group may, for example, be labile under acidic pH conditions. The pH sensitive or acid-labile bond may, for example, include a carboxydimethyl maleate, a hydrazine, an imine, an acetal, an oxime, a silyl ether, a cis-asonityl, a ketal or another pH or acid-labile bond or linkage. Use of a labile bond that is sensitive to acidic conditions may be used to cleave the pendant group in, for example, an acidic tumor environment. In a number of embodiments, the labile linking group is sensitive to reductive such as a disulfide bond. In a number of embodiments, the hydrolytically labile group includes an ester group, an orthoester group, a thioether-ester group, an anhydride group, an amide group (for example, peptide groups), or a carbonate group. ROS-sensitive labile bonds or linkages include, for example, a thioketal bond. An enzyme or protease-sensitive bond or linkage includes, for example, a protease cleavable peptide including the sequence CGLDD which is labile in response to the presence of matrix metalloproteinases MMP-2 or MMP-9.

Figure 3A:
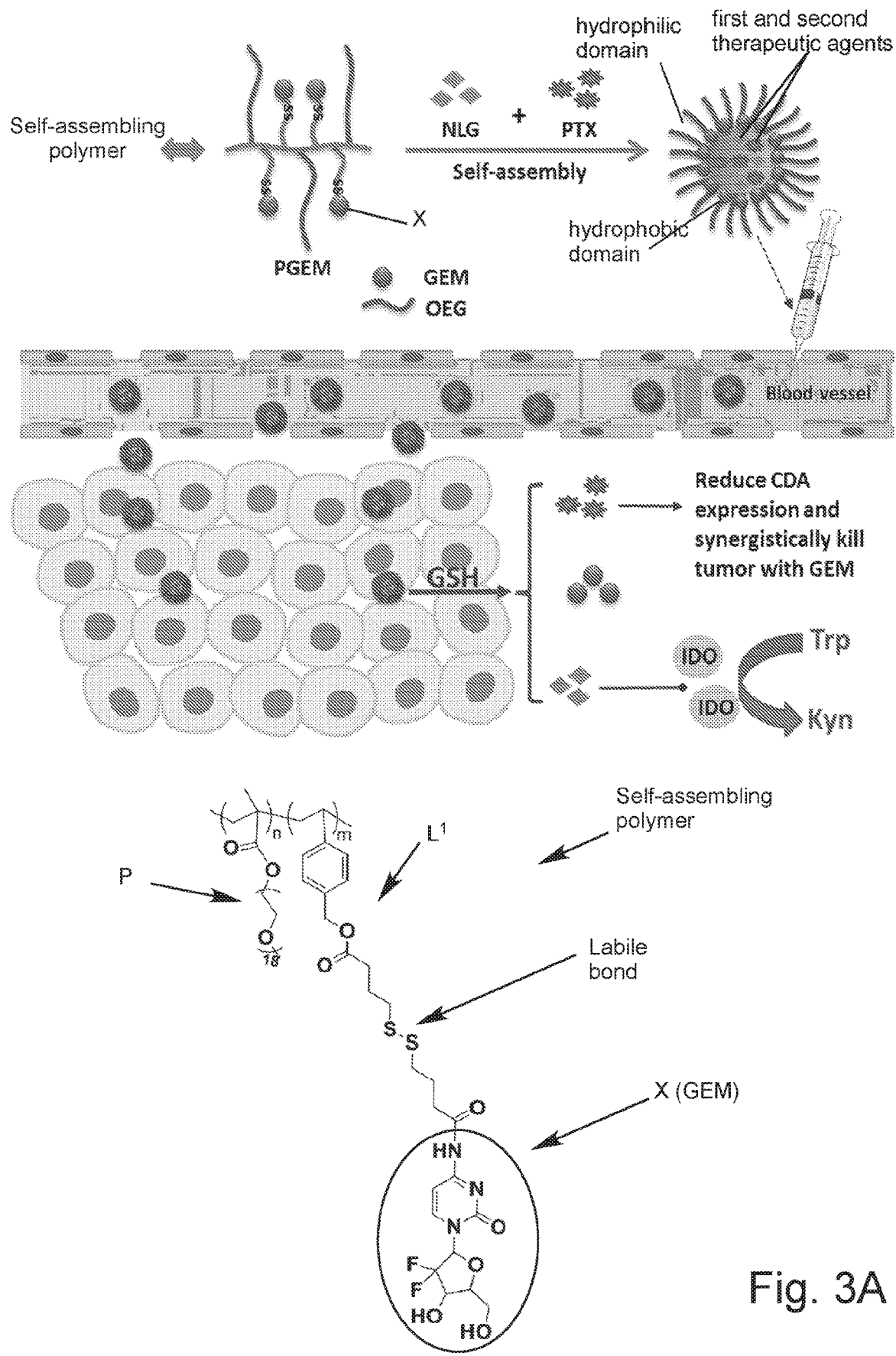
FIG. 3A sets forth an idealized schematic representation of multiple therapeutic agents, compounds or drugs loaded onto a micelle carrier structure formed with a plurality of the polymers hereof.

FIG. 3A sets forth an idealized schematic representation of multiple therapeutic agents, compounds or drugs (that is, first compound, second compound, etc., which are, for example, independently anticancer compounds, antiviral compounds etc. as described in further detail below) loaded onto a micelle carrier structure formed with a plurality of the polymers hereof. As used herein, a therapeutic agent, compound or drug is a biologically active substance which has an effect on the body (for example, a medicinal or therapeutic effect, an intoxicating effect, a performance enhancing effect or another effect). A therapeutic agent may, for example, be an antibody, an antibiotic, an antiviral, an antimycotic, an anticancer agent, an immunomodulating agent, a chemotherapeutic agent, an anti-rejection agent, an analgesic agent, or an anti-inflammatory agent. Small molecule drugs suitable for use herein include, but are not limited to JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl)oxymethyl-5-isopropylisoxazole), rose bengal, epigallocatechin gallate, simvastatin, curcumin, indomethacin, JQ1, I-BET 151, I-BET 762, resiquimod, riluzole, tamoxifen. NLG-919 (an indoleamine 2,3-dioxygenase (IDO) pathway inhibitor), sunitinib, imatinib, erlotinib, gefitinib, cetuximab, a c-Myc inhibitor such as 10058-F4 (5-[(4-ethylphenyl)methylene]-2-thioxo-4-thiazolidinone), cladribine, fludarabine, nelarabine, troxacitabine, capecitabine, 2'-fluoro-2'-deoxyadenosine, acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, and/or 9-deazaadenosine Without limitation to any mechanism, and with reference to FIG. 3A, it is hypothesized that an inwardly oriented hydrophobic domain is created during micelle formation via the hydrophobic backbone of the polymers hereof, which may orient via intrachain hydrophobic interactions to assume a folded conformation. Pendant aromatic groups, when present, may increase hydrophobicity and assist in forming the hydrophobic domain and in π-π interactions with one or more hydrophobic therapeutic or other compounds loaded within the hydrophobic domain. It was further hypothesized that an outwardly oriented hydrophilic domain was formed by the hydrophilic polymer side chains.

Figure 3B:
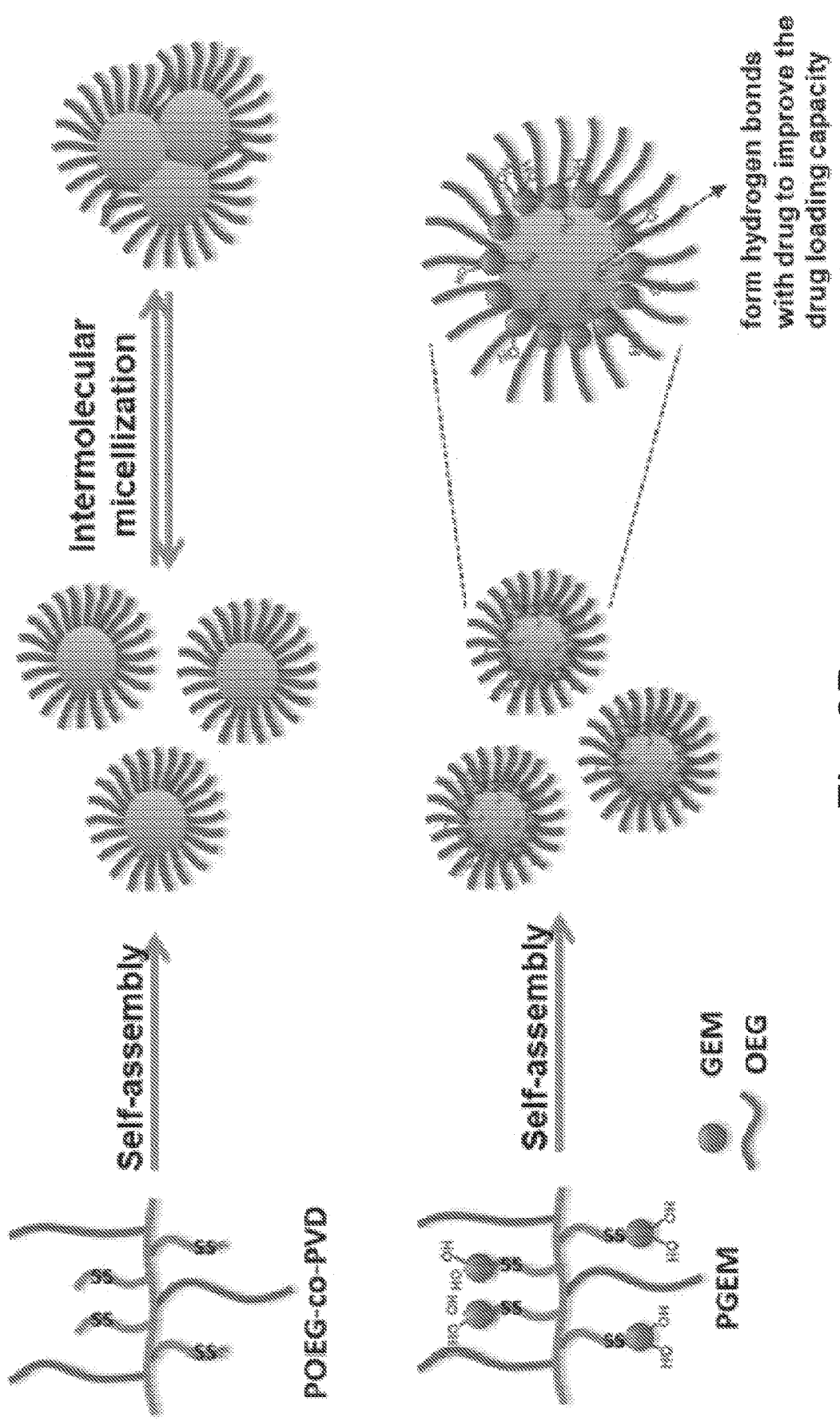
FIG. 3B illustrates schematically a possible mechanism for micelle aggregation with POEG-co-PVD polymers compared to the formation of small micelles and improved drug loading with PGEM polymer.

Without limitation to any mechanism, and with reference to FIG. 3B, the formation of relatively large micelles by prior amphiphilic polymers might be explained by multimicelle aggregates, in which the small micelles formed at the initial stage are not stable enough and quickly aggregated into larger multimicelle aggregates through intermicellar interactions. For the amphiphilic polymers hereof, pendant groups including multiple hydroxyl groups in the interface may form hydrogen bonds with the aqueous surroundings to stabilize relatively small micelles. This mechanism may also explain why the small micelles formed by the amphiphilic polymers hereof exhibit high drug loading capacity and excellent stability. The hydrophobic core (for example, formed from multiple benzyl or other aryl rings and the hydrophobic backbone) may encapsulate hydrophobic agents through 71-71 stacking and hydrophobic interaction. It is hypothesized that some hydroxyl groups oriented inside the micelle core may also form hydrogen bonds with drugs to further enhance the drug loading capacity and stability.

The covalently attached pendant groups X including a plurality of hydroxyl groups may be biologically active groups (for example, therapeutic agents). In the case that the group X is biologically active, it may desirable that the group X be attached via a labile bond as described above (that is, $L^1$ may include a labile bond) to improve biological activity. If X is inert or inactive, it may, for example, be attached via a stable bond (that is, a bond that is not readily cleavable or labile in vivo). The pendant groups X of a polymer hereof (which may be the same or different throughout the polymer) may be hydrophilic. The micelles formed from the polymers hereof thus may deliver both hydrophobic (loaded into structures such as micelles formed by the polymers hereof) and hydrophilic therapeutic (or other) agent (covalently attached to the polymers hereof), which has been very difficult to effect prior to the present compositions.

In a number of embodiments, polymers hereof include a polyol group X which is a sugar or a nucleoside/nucleoside analogue. Many nucleoside analogues, such as gemcitabine, azacitidine and cytarabine, are common drugs used in the treatment of, for example, cancer. However, the rapid elimination of these drugs and their non-specific distribution often leads to side effects, low therapeutic efficacy and resistance. Conjugation of nucleoside analogues to the amphiphilic polymers hereof improves the bioavailability of those therapeutic compounds or drugs. Moreover, these nucleoside analogues-conjugated polymers hereof can serve as platforms for delivery/co-delivery of a variety of hydrophobic drugs. In a number of embodiments, the polyol group has a molecular weight of no greater than 1000.

Nanoparticles formulated from polymers hereof may, for example, be prepared by a facile film hydration method, and have small diameters/size (for example, less than 100 nm, no greater than 50 nm, no greater than 30 nm, no greater than 20 nm, in the range of 10-20, or in the range of 10-30 nm), high drug loading capacity (for example, 28% for paclitaxel) and excellent stability. In a number of embodiments, the drug loading capacity is in the range of 4-30% by weight, in the range of 8-30% by weight, or in the range of 8-20% by weight. In vivo data shows that formulations hereof significantly improved therapeutic effect compared to free drugs or corresponding free drug combinations. Moreover, many formulations hereof show immunostimulatory effect which contributes to the overall anti-tumor activity.

Figure 4:
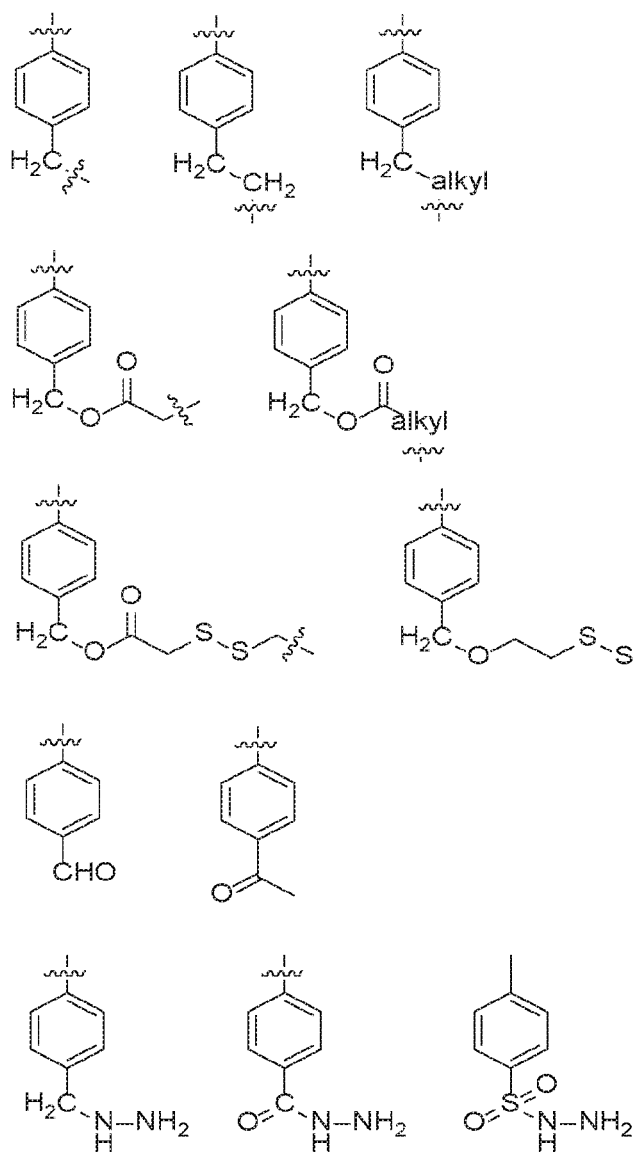
FIG. 4 illustrates representative linker groups for $L^1$ of FIGS. 1 and 2.

As described above, in a number of embodiments, $L^2$ may include a labile bond. For example, after delivery to a target region (for example, into tumor cells), the hydrophilic polymer may be cleaved from the backbone, causing the micelles to disassemble, thereby facilitating release the loaded or encapsulated drugs. Representative linker groups for $L^1$ and $L^2$ are, for example, set forth in FIGS. 4 and 5, respectively.

In a number of representative embodiments, carriers and formulations hereof are effective in the treatment of, for example, pancreatic cancer. As one of the most difficult-to-treat cancers, pancreatic cancer is projected to become the second leading cause of cancer-related deaths by 2030. The standard chemotherapeutic drug for the first-line treatment of pancreatic cancer is gemcitabine (sometimes referred to as GEM), which is a cytidine analogue working through the inhibition of DNA replication. However, limited clinical benefits were achieved because of its rapid clearance through cytidine deaminase (CDA) metabolism, as well as poor vascular permeability. To improve the outcome of treatment, combination of GEM with other chemotherapies or targeted therapies (such as nab-paclitaxel, cisplatin and erlotinib) has been evaluated in preclinical and clinical studies. Increasing evidence indicates that paclitaxel (PTX), in addition to its direct cytotoxic effect on tumor cells, could reduce CDA expression and increase GEM accumulation in the tumors, leading to a synergistic tumor killing effect with GEM. In addition, treatment with PTX and/or GEM can stimulate an antitumor immune response through presentation of antigens released from dying tumor cells or directly killing immunosuppressive cells, which also contributes to the overall antitumor activity.

However, the overall success remains unsatisfactory as a result of various negative feedback mechanisms in the highly immunosuppressive pancreatic tumor microenvironment (TME), which assist tumors to evade normal immune surveillance, such as immune checkpoints cytotoxic T-lymphocyte-associated antigen 4 (CTLA4) and programmed cell death protein 1 (PD1). Indoleamine 2, 3-dioxygenase (IDO) is another well-characterized immunosuppressive enzyme that is overexpressed in pancreatic cancer. Evidence has shown that the high expression of IDO is correlated with a worse prognosis in pancreatic cancer patients. IDO works through the degradation of tryptophan into kynurenine, which is toxic to effector T cells and induces recruitment of T regulatory cells (Treg), resulting in the suppression of anti-tumor immune responses. Thus, inhibition of IDO pathway combined with chemotherapy represents an attractive strategy for the treatment of pancreatic cancer. NLG919 is a potent IDO1 inhibitor with a low $EC_{50}$. The $EC_{50}$ is the concentration which induces a response halfway between the baseline response and the maximum response after a specified exposure time and is commonly used as a measure of a drug's potency. Because of its poor solubility, limited oral bioavailability and distinct physical properties from chemotherapeutic agents, it is difficult to co-deliver NLG919 and chemotherapeutic agents to tumors.

An NLG919 prodrug (in a micellular system of PEG2K-Fmoc-NLG) has been developed as a dual-functional carrier to encapsulate PTX for combination treatment. See, for example, United States Patent Application Publication No. 2018/0214563. It was found that PTX synergized with NLG919 in inhibiting tumor growth by directly killing tumor cells and simultaneously enhancing anti-tumor immune response in breast tumor models. That system is well suited for codelivery of water-insoluble, hydrophobic drugs. However, co-delivery of hydrophobic drug such as PTX with water-soluble drug like GEM presents further difficulties. Moreover, as described above, many previous micellular systems have a relatively large hydrodynamic size, which may hinder penetration into the tumors that are poorly vascularized and enriched with stroma such as pancreatic tumor.

It has been well established that many tumor vessels are leaky with larger pore sizes compared with normal vessels, which allow particles of nanosize range (4-200 nm) to selectively accumulate at tumor tissues. However, the cutoff size of pores for tumor vasculature varies significantly with the tumor types. Pancreatic cancer is known to be poorly vascularized with much smaller pore sizes (~50-60 nm) compared to other cancer types. Additionally, pancreatic cancer has dense stroma that further limits the penetration of large-sized nanoparticles. Previous studies have found only nanoparticles smaller than 50 nm could penetrate poorly permeable pancreatic tumors. It has also been reported that nanoparticles of small sizes (~10 nm) exhibited superior tumor penetration compared to larger nanoparticles in other tumor models. However, small-sized nanoparticles often have limitations in drug loading with lower drug loading capacity and efficiency compared to larger nanoparticles. It remains a challenge to develop a small-sized nanocarrier that is capable of deep tumor penetration yet highly effective in codelivery of different drugs (such as GEM/PTX and NLG) for pancreatic cancer immunochemotherapy.

Once again, because of the biological complexity and highly immunosuppressive TME of pancreatic cancer, development of new combinations of immunotherapeutic agents and chemotherapeutics, as well as the related formulations for pancreatic cancer immunochemotherapy is desperately needed. Compared to free drug combinations, engineering the combined drugs in a single nanocarrier can improve the pharmacokinetics and biodistribution profiles, decrease side effects and allow the simultaneous delivery of multiple drugs to tumor site in their optimal dosage, leading to the improved synergistic therapeutic effect.

In a representative embodiment hereof, an "ultra-small" nanocarrier assembled from redox-responsive gemcitabine (GEM)-conjugated polymer POEG-co-PVDGEM (PGEM) is described to, for example, co-deliver the IDO inhibitor NLG919 and the chemotherapeutic drugs PTX and GEM into, for example, a pancreatic tumor for immunochemotherapy. The GEM-conjugated polymer (PGEM) nanocarrier was able to co-load a wide variety of hydrophobic drugs with high loading capacity and excellent stability. The PGEM nanocarrier could efficiently penetrate into the tumor core and inhibit tumor growth. It was shown that incorporation of PTX into the PGEM carrier downregulated the CDA expression, and synergistically inhibited the tumor growth with the co-delivered GEM. Incorporation of NLG into the carrier induced a more immunoactive tumor microenvironment with increased IFN-γ+ CD4+ and IFN-γ+ CD8+ T cells and decreased Treg cells, and thereby enhanced the therapeutic effect. Co-delivery of GEM/PTX/NLG through the nanocarrier further enhanced the therapeutic effect with tumor inhibition rate as high as 90.4%, which demonstrated significant potential as an effective combination regimen for pancreatic cancer immunochemotherapy.

Once again, particle size of an injectable carrier is a very important physicochemical parameter to be considered because it plays a vital role in the cellular uptake, biodistribution and tumor penetration. As also described above, it has been reported that nanoparticles with diameter range of 4-200 nm have long circulation time and can efficiently accumulate in the tumors as a result of an enhanced permeability and retention (EPR) effect. Nanoparticles less than 4 nm are rapidly excreted by the kidney, while nanoparticles larger than 200 nm tend to be taken up by the reticuloendothelial system (RES). Moreover, accumulating evidence indicates that nanomedicines with small sizes (10~ 30 nm) exhibit superior tumor penetration and enhanced anti-tumor activity, particularly for pancreatic cancer. The representative PGEM carrier hereof exhibited a desirable particle size (approximately 13 nm) to avoid RES uptake and renal excretion, which is also beneficial for accumulation and penetration in pancreatic tumor tissues (<50 nm).

Furthermore, the representative PGEM carriers hereof overcome the limitations of ultra-small polymeric carriers in drug loading. Generally, it is believed that reduction in the size of polymeric micelles can be achieved by increasing the hydrophilic/hydrophobic block ratio. However, at such a high ratio, a thick shell with a "tiny" core will be generated, leading to the low encapsulation capacity and poor stability of the drug-loaded micelles. Surprisingly, the representative PGEM carriers hereof were able to load a wide variety of hydrophobic agents such as curcumin, NLG919, doxorubicin, dasatinib and c-Myc inhibitor 10058-F4 with excellent stability and high loading capacity. In the case of loading PTX, a capacity of 24.2 wt. % was achieved. Moreover, the PGEM carriers hereof enable a high co-loading of multiple drugs with distinct properties, such as hydrophilic GEM and hydrophobic PTX/NLG. The conjugation of hydrophilic GEM molecules to the POEG-co-PVD polymer led to the significantly decreased particle size (from approximately 160 nm to approximately 13 nm), but the loading capacity and formulation stability was improved.

Once again, CDA is overexpressed in pancreatic tumor, which plays a key role in GEM resistance. Approximately 80% amount of administered GEM will be metabolized by extracellular and intracellular CDA into the inactive form 2',2'-difluorodeoxyuridine (dFdU), which largely limits the therapeutic efficacy of GEM. It has been shown that PTX could reduce CDA protein levels instead of RNA levels, possibly mediated by PTX-induced ROS, and the decreased CDA expression resulted in higher accumulation of active GEM form in tumors. Consistent with these work, our data demonstrated that PTX synergized with GEM in killing PANC02 cells, and incorporation of PTX in the PGEM carrier led to significant downregulation of CDA expression. This contributed to the enhanced anti-tumor effect of PTX/PGEM compared to PGEM in vitro and in vivo.

On the other hand, a variety of immunosuppressive mechanisms and molecules like TGF-β, galectin-1 and IDO have been identified in the pancreatic TME, which opens new windows for pancreatic cancer immunochemotherapy. Among them, IDO is an attractive immunotherapy target, which is overexpressed in pancreatic cancer while not expressed in healthy pancreatic tissue. IDO inhibitor indoximod combined with chemotherapeutics including nab-PTX and GEM for advanced PDAC has moved into phase Ib trial. NLG919 is another potent IDO inhibitor with distinct mechanism and lower $EC_{50}$. NLG919 formulated in the PGEM carrier maintained its biological effect in inhibiting the IDO activity, and co-delivery of PTX with NLG didn't affect the IDO inhibitory effect of NLG. Immunological analysis demonstrated that NLG/PGEM treatment generated a more immunoactive TME with increased $CD4^+/CD8^+$ T cells and IFN-γ positive $CD4^+/CD8^+$ T cells compared with PGEM. Since incorporation of NLG didn't improve the cytotoxicity of PGEM, the improved therapeutic effect of NLG/PGEM with respect to PGEM is mainly attributed to the enhanced anti-tumor immune response. PGEM itself could also boost anti-tumor immune response with less immunosuppresive Treg cells and more production of IFN-γ, indicating PGEM as an immunostimulatory carrier. GEM has been reported to suppress Treg cells, depending on the dosage. PTX/PGEM shows better effect in activating the immune system compared with Taxol+GEM combination, which may, for example, be a result of the more effective delivery of PTX and GEM into the tumors via the carriers hereof Compared to NLG/PGEM, co-delivery of PTX and NLG via PGEM didn't make much change to the immune tumor microenvironment, however, contributed to the best therapeutic efficacy, suggesting the desirability of PTX/NLG combination.

FIG. 3A schematically illustrates a proposed mechanism for operation of the representative PGEM carriers hereof. The PGEM micelles co-loaded with PTX and NLG efficiently penetrate into tumor tissues as a result of their small particle size. PGEM showed tumor killing effect and immunostimulatory effect itself. PTX and NLG were readily released from PGEM carrier in response to intracellular GSH. The released PTX could reduce CDA expression and synergize with GEM in killing tumors. The released NLG919 further reverses the IDO1 function and increase T cell responses against tumor.

In the representative studies, as further discussed below, it is shown that a PTX/NLG/PGEM regimen provided by the PGEM carriers hereof is highly efficacious for the treatment of pancreatic cancer in PANC02 cell line model. PANC02 is a unique tumor model with high resistance to almost all the well-known clinically chemotherapeutic agents, which could be used as a close mimic of human pancreatic cancer.

Figure 6:
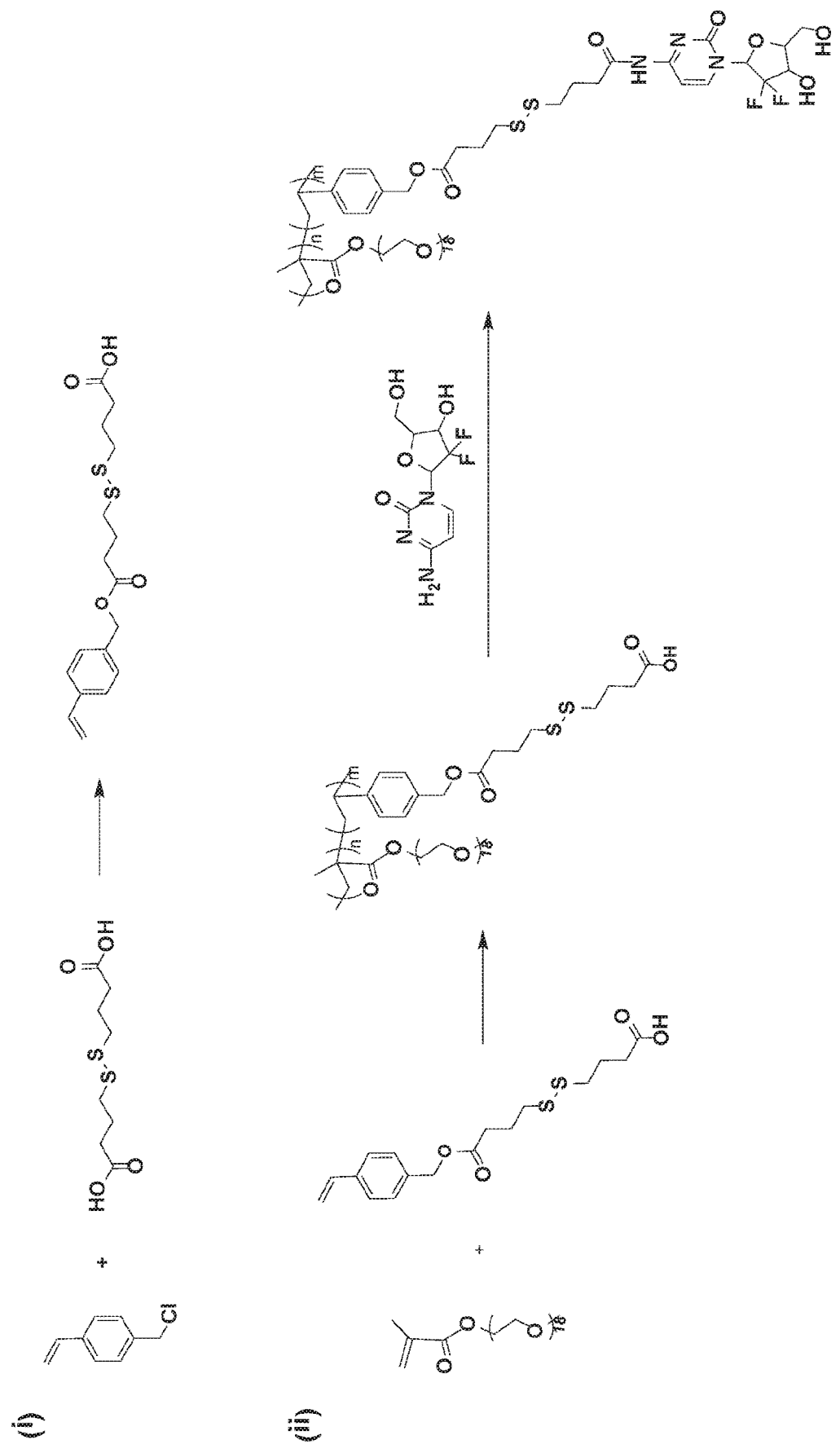
FIG. 6 illustrates a synthetic scheme for POEG-co-PVD-GEM polymers hereof.

As shown in FIG. 6, vinyl benzyl monomers with disulfide linkage (VD monomer) were synthesized via reaction of vinylbenzyl chloride and 4, 4'-Dithiodibutyric acid. Then, POEG-co-PVD polymer was synthesized by RAFT copolymerization of VD monomer and OEG950 monomer. POEG-co-PVDGEM polymer was obtained by conjugating GEM to the POEG-co-PVD polymer backbone using, for example, an EDC/HOBt coupling reaction as known in the chemical arts.

The structures of VD monomer, POEG-co-PVD and POEG-co-PVDGEM polymers were characterized by $^1H$ NMR. For POEG-co-PVD polymer, the average degree of polymerization (DP) of the OEG950 monomer was calculated to be 9 according to the conversion of OEG950 monomer at the end of the polymerization. The DP of the VD monomer was determined to be 23 by comparing the intensities of $I_c$ and $I_d$. After conjugation of GEM to POEG-co-PVD polymer, protons peaks corresponding to GEM were observed in the $^1H$ NMR spectrum, and the number of GEM units per polymer molecule was determined to be 8 by comparing the intensities of $I_c$ and $I_d$. GEM loading capacity was also determined by HPLC-UV analysis via the alkaline hydrolysis method. A gemcitabine loading in the POEG-co-PVDGEM polymeric carrier was determined to be 8.9% w/w.

The molecular weight and distributions of the POEG-co-PVD and POEG-co-PVDGEM polymers were also determined by GPC. The number average molecular weight $M_n$ determined by GPC was 11600 for POEG-co-PVD and 9200 for POEG-co-PVDGEM, respectively. Both polymers showed low polydispersity of 1.12. It is noted that $M_n$ of POEG-co-PVDGEM determined by the GPC was decreased after GEM conjugation to the POEG-co-PVD polymer backbone. It is well known that GPC separates the polymers by hydrodynamic size instead of molar mass. So the decrease in measured polystyrene-relative molecular weight of POEG-co-PVDGEM indicated a compaction of the polymer chain in THF after GEM conjugation. The GPC and NMR results indicated the successful synthesis of POEG-co-PVDGEM (PGEM) copolymers with defined and controllable structure.

Both POEG-co-PVD and PGEM polymers were able to form nanoparticles in the aqueous solution via a simple film hydration method. POEG-co-PVD micelles showed a diameter of 161 nm. After GEM conjugation, the PGEM polymer formed smaller nanoparticles with a diameter decreased to 13.1 nm, indicating that the GEM structure played an important role in forming the small sized nanoparticles.

TEM image of PGEM nanoparticle demonstrated a spherical morphology with average diameter of 12.5±2.0 nm, which is consistent with the DLS measurement. The critical micelle concentration of PGEM was evaluated by fluorescence spectrometry using nile red as a probe. The critical micelle concentration value (CMC; the concentration above which micelles form) of the PGEM micelles was 0.0072 mg/mL, which provided a good colloidal stability after dilution in the blood circulation.

PTX-loaded micelles were prepared via the film hydration method with different carrier/drug mass ratios. As shown in Table 1, the PTX loading capacity was increased when decreasing the mass ratio of carrier/PTX, and a surprisingly high loading capacity of 24.2% was achieved. All of the formulations exhibited very small particle sizes, which are suitable to. for example, penetrate into pancreatic tumor tissues. The formulation stability at room temperature was also evaluated by measuring the size changes. With PTX loading capacity of around 5%, the formulation could be stable for more than 20 days without observation of any precipitates. Moreover, the micelle solutions were stable after repeated lyophilization.

TABLE 1

Characterization of blank PGEM micelles and PTX-loaded micelles.

| Micelles | Mass ratio (mg:mg) | Size (nm)$^a$ | PDI$^b$ | DLC (%)$^c$ | DLE (%)$^c$ | Stability$^d$ |
|---|---|---|---|---|---|---|
| PGEM | — | 13.14 | 0.169 | | | |
| PGEM:PTX | 20:1 | 13.95 | 0.136 | 4.6 | 97.2 | 20 d |
| PGEM:PTX | 10:1 | 14.90 | 0.151 | 8.3 | 92.1 | 10 d |
| PGEM:PTX | 5:1 | 17.77 | 0.227 | 14.8 | 88.7 | 48 h |
| PGEM:PTX | 2.5:1 | 23.07 | 0.265 | 24.2 | 84.6 | 30 h |

$^a$Measured by dynamic light scattering particle sizer.
$^b$PDI = polydispersity index.
$^c$PTX loading capacity.
$^d$Formulation stability at room temperature.

Figure 7:
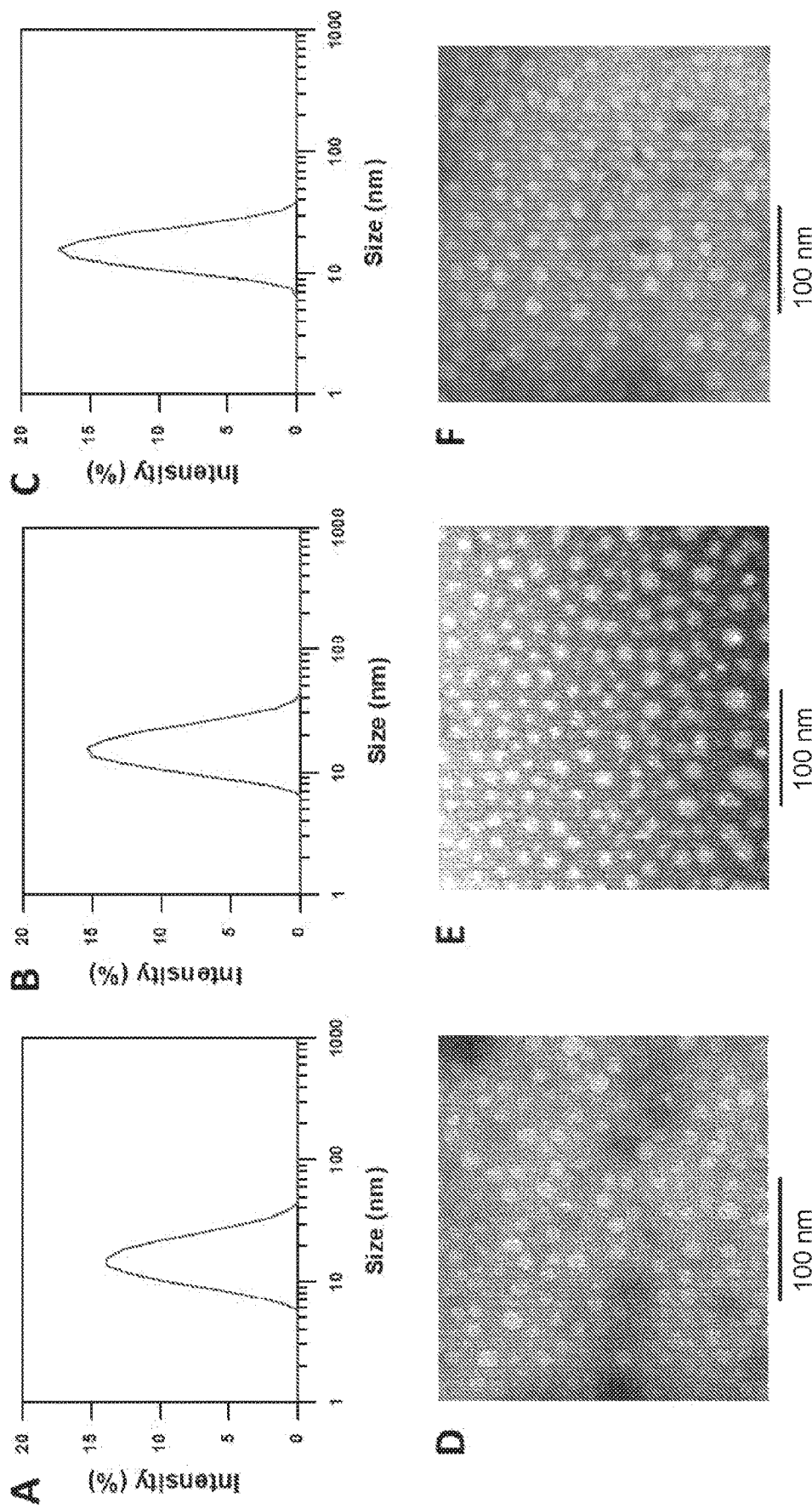
FIG. 7 illustrates characterization of drug-loaded micelles, wherein panel A illustrates particle size of PTX-loaded PGEM micelles; panel B illustrates particle size of NLG-loaded PGEM micelles; panel C illustrates particle size of PTX/NLG-coloaded PGEM micelles; panel D illustrates a TEM image of PTX-loaded PGEM micelles; panel E illustrates a TEM image of NLG-loaded PGEM micelles; panel F illustrates a TEM image of PTX/NLG-coloaded PGEM micelles using negative staining, and wherein the scale bar is 100 nm in panels D through F and, in the DLC studies, PTX and NLG are 3.8% and 7.4%, respectively.

In addition to PTX, PGEM carrier was able to load a variety of other drugs such as curcumin, NLG919, doxorubicin, dasatinib and c-Myc inhibitor 10058-F4 (see Table 2 below), some of which are difficult-to-formulate compounds. All these micellular formulations showed ultra-small size, high drug loading capacity and excellent stability. Moreover, PGEM carrier could co-encapsulate two different drugs, such as PTX and NLG919. The size distribution and morphologies of PTX-loaded micelles, NLG-loaded micelles or PTX/NLG-co-loaded micelles were characterized by DLS and TEM (see FIG. 7). All of these formulations showed spherical morphologies with uniform particle size of around 15 nm.

TABLE 2

Characterization of PGEM micelles loaded with various drugs.

| Micelles | Mass ratio (mg:mg) | Size (nm)$^a$ | PDI$^b$ | DLC (%)$^c$ | DLE (%)$^c$ | Stability$^d$ |
|---|---|---|---|---|---|---|
| PGEM:Cur | 10:1 | 15.50 | 0.195 | 8.7 | 96.1 | 18 d |
| PGEM:NLG | 10:1 | 14.60 | 0.108 | 8.3 | 91.5 | 6 d |
| PGEM:DOX | 10:1 | 14.41 | 0.311 | 8.5 | 93.7 | 8 d |
| PGEM:Das | 20:1 | 13.27 | 0.126 | 4.4 | 93.4 | 18 d |
| PGEM:10058-F4 | 20:1 | 13.82 | 0.120 | 4.3 | 90.6 | 4 d |

Figure 8A:
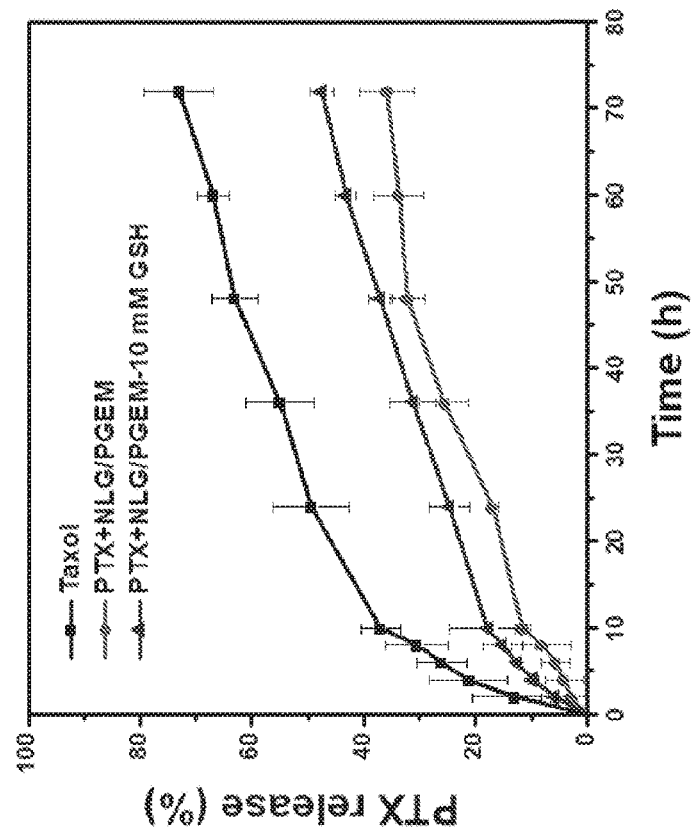
FIG. 8A illustrates the cumulative PTX release profile from PTX/NLG-coloaded PGEM micelles, wherein PBS containing 0.5% (w/v) TWEEN® 80 (a nonionic surfactant and emulsifier derived from polyethoxylated sorbitan and oleic acid) was used as the release medium, and values reported are the means±SD for triplicate samples.
Figure 8B:
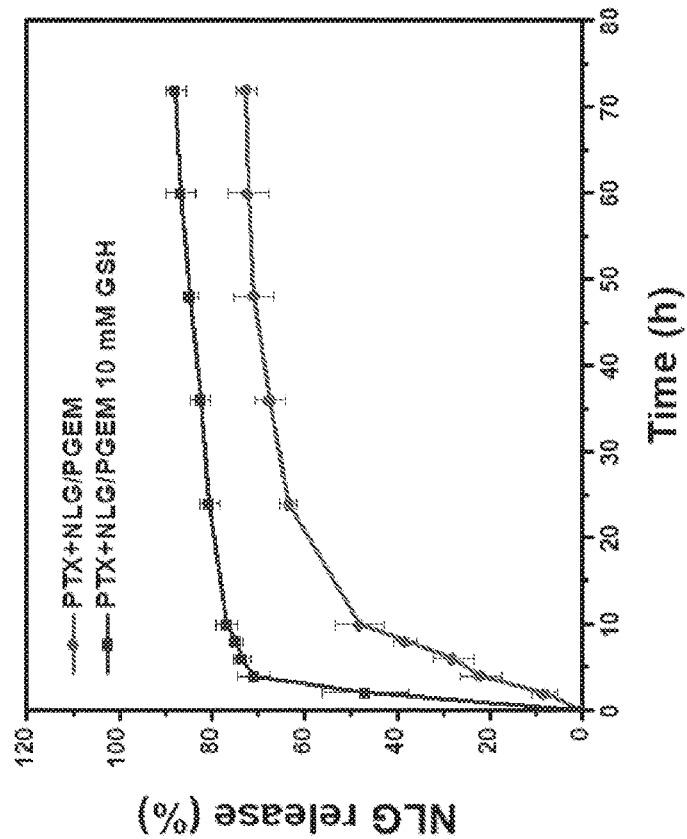
FIG. 8B illustrates the cumulative NLG release profile from PTX/NLG-coloaded PGEM micelles, wherein PBS containing 0.5% (w/v) TWEEN 80 was used as the release medium, and values reported are the means±SD for triplicate samples.

The PTX and NLG release profiles of PTX+NLG/PGEM micelles were evaluated with a dialysis method. As shown in FIG. 8A, Taxol showed faster release of PTX and almost 75% of PTX was released within 72 h. In comparison, PTX+NLG/PGEM micelles showed more favorable release kinetics of PTX, and only 35% of PTX was slowly released within 72 h. In the presence of 10 mM GSH, PTX release from PTX+NLG/PGEM micelles was promoted and 47% of PTX was released at 72 h. The NLG release profile of PTX+NLG/PGEM micelles with and without 10 mM GSH is shown in FIG. 8B. Around 72% of NLG was released from PTX+NLG/PGEM micelles at 72 h, while 84% of NLG was released with 10 mM GSH. These results indicated that highly redox environment in the tumor cells could promote the release of PTX and NLG from the carrier as the result of the cleavage of disulfide linkage by intracellular GSH.

The combination effect of free GEM and PTX was studied in two pancreatic cancer cell lines PANC02 and H7. Compared to single drug, combination of PTX and GEM significantly improved tumor cell killing effect. The combination index (CI) in PANC02 and H7 cells was calculated to be 0.5 and 0.6, respectively, suggesting synergistic effect (CI<1) of PTX and GEM in both cells.

Figure 9B:
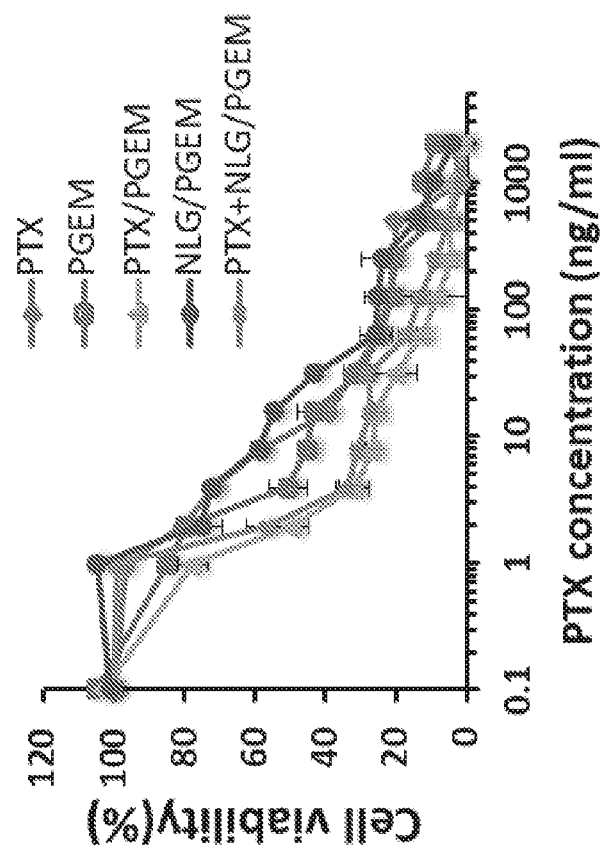
FIG. 9B illustrates an MTT cytotoxicity study of various formulations in a PANC02 cell line, wherein cells were treated with different micelles for 96 h and values reported are the means±SD for triplicate samples.
Figure 9A:
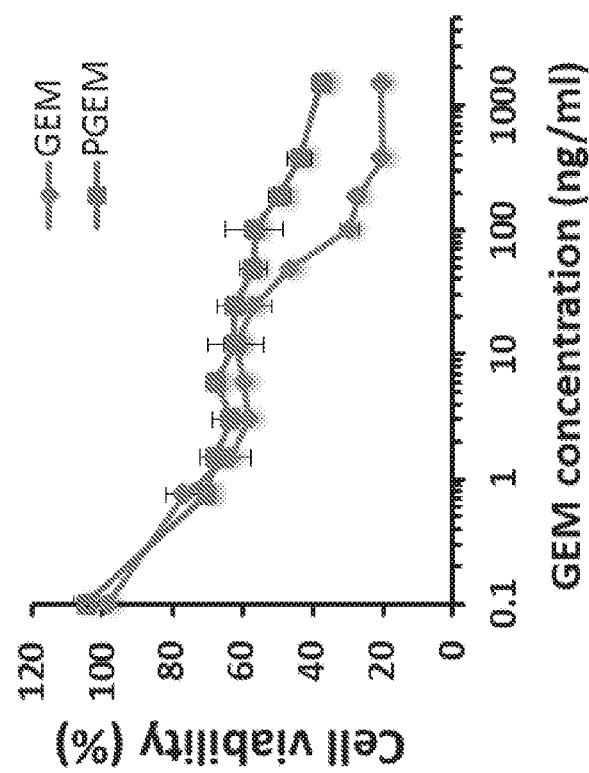
FIG. 9A illustrates an MTT cytotoxicity assay of PGEM prodrug micelles in a PANC02 cell line with free GEM as the control, wherein cells were treated with different micelles for 96 h and values reported are the means±SD for triplicate samples.

The cytotoxicity of PGEM prodrug micelles were examined in PANC02 cells. It can be seen from FIG. 9A that both free GEM and PGEM exhibited a concentration-dependent cell killing effect. The $IC_{50}$ of PGEM prodrug micelles was higher than that of free GEM in PANC02 cells, which might be a result of the incomplete cleavage of GEM from the PGEM polymer in the cells within the short period time of treatment. The half maximal inhibitory concentrationor $IC_{50}$ is a measure of the effectiveness of a substance in inhibiting a specific biological or biochemical function. The cytotoxicity of various nanoformulations was also evaluated in PANC02 cells (see FIG. 9B). NLG-loaded micelles showed similar cytotoxicity as compared to PGEM carrier. PTX-loaded micelles and PTX/NLG co-loaded micelles showed better cytotoxicity compared to free PTX, PGEM and NLG-loaded micelle. Similar trends were shown for various formulations in H7 cells, which indicated that incorporation of NLG didn't change the cell killing effect of PGEM, while incorporation of PTX in the formulation enhanced the cell killing effect.

As described above, CDA is overexpressed in pancreatic cancer, which mediates the metabolism of cytidine analogue drugs, such as gemcitabine of GEM, leading to the resistance to treatment with these drugs. Thus, reducing the CDA expression provides a new therapeutic window for pancreatic cancer. We examined the CDA expression in PANC02 cells treated with various formulations by western blot. CDA expression was not altered by free GEM and PGEM compared with the control group, while CDA expression was significantly downregulated after treatment with PTX/PGEM or PTX/NLG/PGEM formulations. Moreover, an NLG/PGEM formulation also led to some reduction in CDA protein levels.

Figure 10:
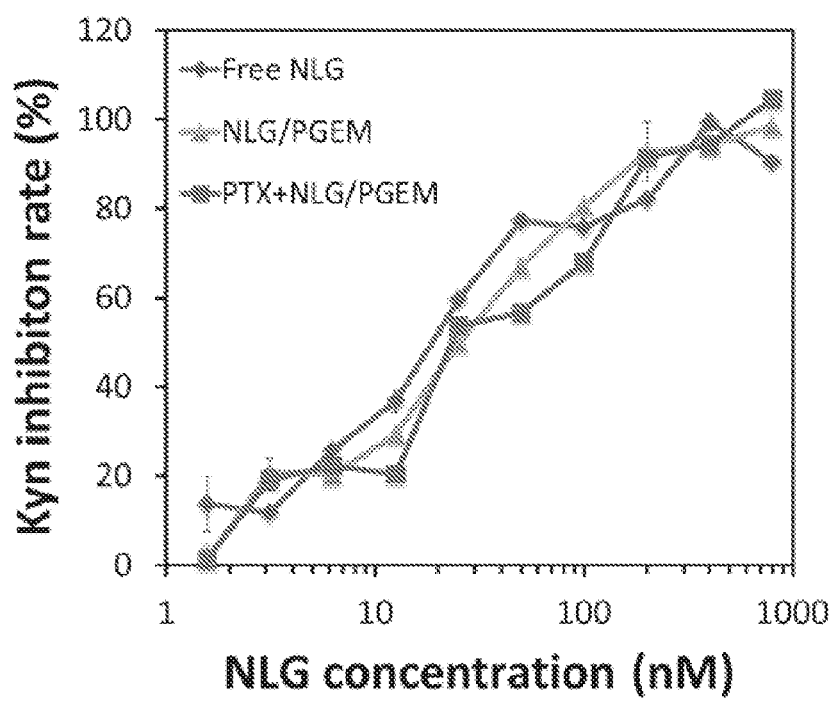
FIG. 10 illustrates in vitro inhibitory effect of IDO activity wherein PANC02 cells were treated with IFN-γ together with free NLG919, PTX/PGEM, NLG/PGEM and PTX+NLG/PGEM and wherein Kynurenine (Kyn) in supernatants was measured 2 days later.

The IDO inhibitory activity of the formulation NLG/PGEM and PTX+NLG/PGEM was investigated in PANC02 cells by detecting the decreased levels of kynurenine (Kyn) through a colorimetric assay. FIG. 10 illustrates the kyn inhibition rate in PANC02 cells after the treatment with free NLG, NLG/PGEM and PTX+NLG/PGEM with various NLG concentrations. All the compositions inhibited the IDO function in a NLG concentration dependent manner. NLG/PGEM and PTX+NLG/PGEM formulations showed similar IDO inhibitory effect compared with free NLG919.

In vivo biodistribution of PGEM micelles was investigated by near-infrared fluorescent optical imaging in a PANC02 model with POEG-co-PVD nanoparticles as a control (~160 nm). A highly penetrating hydrophobic fluorescence dye DiR was loaded into the micelles for tissue imaging. DiR signal increased in the tumor regions over time and became the strongest 24 h after the treatment of both micelles. Compared with POEG-co-PVD, PGEM micelles showed lower uptake by liver, spleen and kidney.

It has been reported that nanoparticles with smaller size shows deeper penetration in tumors. Thus, the tumor penetration capability of ultra-small PGEM carriers hereof was determined by florescence imaging in comparison with the larger nanoparticle self-assembled by POEG-co-PVD polymer backbone (~160 nm). Rhodamine and fluorescein was loaded into PGEM carrier and POEG-co-PVD carrier, respectively, as a fluorescence probe. To minimize the individual difference, the two types of dye-loaded nanoparticles were mixed with same amount and co-injected in the same mouse intravenously. Green fluorescence signals from fluorescein/POEG-co-PVD nanoparticles became weaker in the tumor core, while strong red fluorescence signals from rhodamine/PGEM nanoparticles were still clearly observed, which indicated deeper penetration ability of PGEM carrier. To rule out the possibility that the different intensity of fluorophore interferes with the results, we switched the fluorescence probe, and used PGEM carrier to load fluorescein and POEG-co-PVD to load rhodamine. Similarly, fluorescein-loaded PGEM showed higher tumor uptake and deeper tumoral diffusion than rhodamine-loaded POEG-co-PVD.

To further study the combination effect of immunotherapy with chemotherapy in pancreatic cancer, an immunocompetent murine model with PANC02 tumor was used. PANC02 cells were subcutaneously injected into C57BL/6 mice. After 12 days, the tumor-bearing mice were intravenously (IV) injected with saline, PGEM carrier, PTX/PGEM, NLG/PGEM, PTX/NLG/PGEM micelles and Taxol combined with free GEM (see FIG. 11, panel A).

Figure 11:
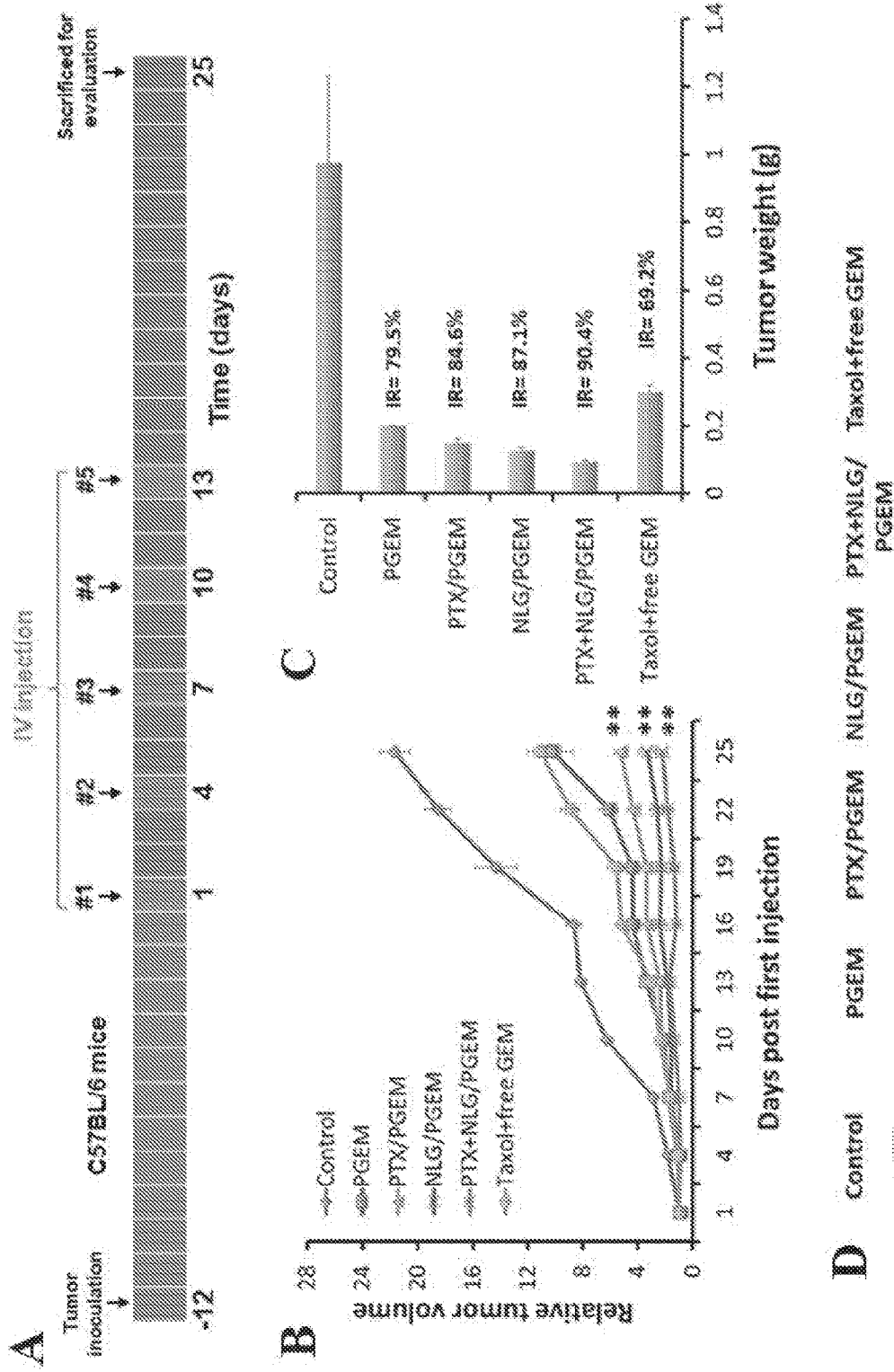
FIG. 11 illustrates in vivo therapeutic effect, wherein: panel A illustrates that PANC02 cells were subcutaneously injected 12 days before treatment of various formulations, including saline, PGEM, PTX/PGEM, NLG/PGEM, PTX+NLG/PGEM and a mixture of taxol and free GEM, wherein five intravenous injections were made every 3 days; panel B illustrates relative tumor volume changes of the mice treated with various formulations; panel C illustrates tumor weights of the mice receiving different treatments and tumor inhibition rate (IR) of various formulations; and panel D illustrates photographs of excised tumors in each treatment group.

PGEM prodrug micelles showed similar anti-tumor activity as the combination group of Taxol and free GEM (see FIG. 11, panel B). PTX/PGEM micelle showed much higher anti-tumor activity than that of PGEM carrier, which was consistent with the in vitro MTT cytotoxicity results (see, FIGS. 9A and 9B). NLG/PGEM micelle showed even higher anti-tumor activity compared to PTX/PGEM micelle, indicating that the introduction of IDO inhibitor NLG919 into PGEM carrier might improve the anti-tumor immune response, which is very important for pancreatic cancer treatment. Among all the formulations, PTX/NLG-coloaded micelles showed the highest anti-tumor activity. The body weights of mice were also monitored, and the mice treated with various formulations didn't show significant changes in body weight. After sacrificing the mice, the tumor weights were measured (ee FIG. 11, panel C). The mice treated with PTX/NLG/PGEM micelles showed the lowest tumor weight and highest tumor inhibition rate (90.4%), which further confirmed its improved therapeutic efficacy over other formulations.

FIG. 11, panel D shows the photographs of extracted tumors after various treatments. The mice treated with PTX/NLG/PGEM micelles showed the smallest size of tumors. In hematoxylin and eosin (H&E) stained images of tumor sections after various treatments (not shown), large nuclei were observed in the tumor cells with saline treatment, while shrunk nuclei were observed in the tumor tissues with other treatments. Among them, the mice treated with PTX+NLG/PGEM showed the widest necrotic range of tumor cells.

The biochemical parameters including serum alanine aminotransferase (ALT), aspartate aminotransferase (AST), creatinine and blood urea nitrogen (BUN) levels were evaluated as indicators of hepatic and renal function. The mice, after treatment with PTX+NLG/PGEM formulation, showed normal level of these parameters, suggesting there was no obvious damage to hepatic and renal functions after treatment with PTX+NLG/PGEM micelle.

The changes in the PANC02 tumor microenvironment following various treatments were investigated by flow cytometric analysis of the immune cell populations in the tumors. No significant changes in the numbers of total $CD4^+$ T cells were observed in the tumors after various treatments compared with the control group. After treatment with PGEM, NLG/PGEM or PTX/NLG/PGEM, the relative numbers of $CD8^+$ T cells in the tumors were significantly increased. Among these groups, the tumor in the NLG/PGEM treatment group showed the highest relative number of $CD8^+$ T cells. Treg cells are a subtype of T cells that contribute to an immunosuppressive microenvironment. All the treatments, except the combination of taxol and free GEM, could significantly decrease the number of Treg cells in the tumor tissues (see FIG. 12A). IFN-γ is a powerful molecule produced by T cells, which plays an important role in eliminating solid tumors [37]. We found that the relative numbers of IFN-γ$^+$ $CD4^+$ T cells (see FIG. 12B) and IFN-γ$^+$ $CD8^+$ T cells (see FIG. 12C) in the tumors were significantly increased after treatment with PGEM, PTX/PGEM, NLG/PGEM or PTX/NLG/PGEM. The PTX/PGEM group showed higher relative numbers of IFN-γ$^+$ $CD4^+$ and IFN-γ$^+$ $CD8^+$ T cells, and lower numbers of Treg cells compared with the combination group of taxol and free GEM. In addition, compared with PGEM, incorporation of NLG in the formulation further increased the numbers of IFN-γ+ $CD4^+$ and IFN-γ$^+$ $CD8^+$ T cells. Overall, our formulations could induce a more immunoactive tumor microenvironment, leading to an enhanced anti-tumor immune response.

The carrier platform hereof is not a GEM-specific or limited system. The carriers hereof may, for example, be formed with many structural analogues of GEM as well as other hydrophilic compounds/drugs. Thus, the carrier system strategy hereof can be extended to co-delivery of multiple distinct hydrophilic and hydrophobic agents for various combination therapies.

Figure 13:
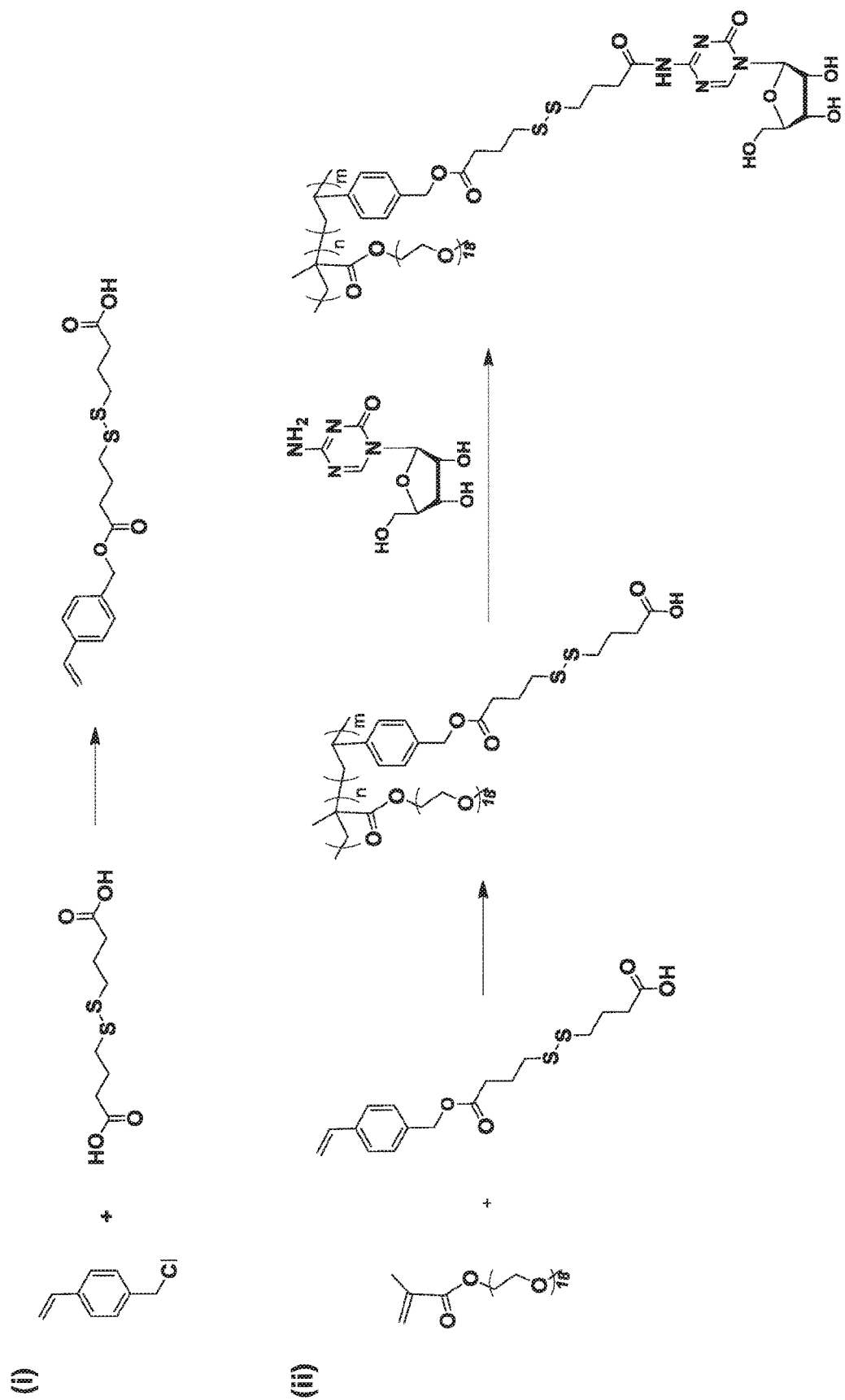
FIG. 13 illustrates a synthetic scheme for an azacytidine-conjugated polymer (PAza).

Other embodiments hereof are described and characterized in FIGS. 13 through 16B. FIG. 13 illustrates a synthetic scheme for an azacytidine-conjugated polymer (PAza). PAza polymer was obtained by conjugating azacytidine to the POEG-co-PVD polymer backbone using, for example, an EDC/HOBt coupling reaction as known in the chemical arts. FIG. 14A illustrates a DLS particle size study and a TEM image of blank PAza micelles, and it shows particle size of approximately 13 nm and spherical morphology, while FIG. 14B illustrates a DLS particle size study and a TEM image of DOX-loaded PAza micelles. The DOX-loaded PAza micelles also showed spherical morphology with a little larger size of 16 nm.

FIG. 15A illustrates a synthetic scheme for the synthesis of 2DG-conjugated polymer (P2DG), wherein 2DG is 2-de-oxy-D-glucose. P2DG polymer was obtained by conjugating 2DG to the POEG-co-PVD polymer backbone using, for example, an EDC/HOBt coupling reaction as known in the chemical arts. FIG. 15B illustrates a DLS particle size study, a TEM image of blank P2DG micelles and a fluorescine intensity study thereof. It showed particle size of approximately 11.48 nm and spherical morphology. In addition, it showed good stability with low critical micelle concentration (CMC, 22.6 mg/L). FIG. 16A illustrates DLC particle size studies for P2DG loaded with PTX (panel A), DOX (panel B), NLG919 (panel C) and sunitinib (panel D). All of these nanoparticles were of small size. FIG. 16B illustrates TEM images of blank P2DG and P2DG loaded with sunitinib (SUN), PTX and a combination of PTX/SUN. All of these nanoparticles exhibited spherical morphologies. These results indicated that P2DG polymer was able to load various bioactive agents such as anti-cancer and/or antiviral agents.

Experimental Examples

Materials. Vinylbenzyl chloride, 4,4'-Dithiodibutyric acid, oligo(ethylene glycol) methacrylate (OEG950 monomer, average $M_n$=950), 4-Cyano-4-(phenylcarbonothioyl-thio)pentanoic acid, 2, 2-Azobis(isobutyronitrile) (AIBN), trypsin-EDTA solution, 3-(4,5-dimethylthiazol-2-yl)-2,5-di-phenyl tetrazolium bromide (MTT) and Dulbecco's Modified Eagle's Medium (DMEM) were all bought from Sigma-Aldrich (MO, U.S.A). AIBN was purified by recrystallization in anhydrous ethanol. 1-hydroxybenzotriazole (HOBT) and 1-(3-dimethylaminopropyl)-3-ethylcarbodiimide HCl (EDC) were purchased from GL Biochem (Shanghai, China). Diisopropylethylamine (DIPEA) was purchased from Acros Organics. Paclitaxel was purchased from AK Scientific Inc. (CA, U.S.A). Doxorubicin hydrochloride salt (DOX HCl) and gemcitabine (GEM) was purchased from LC Laboratories (MA, USA). Fetal bovine serum (FBS) and penicillin-streptomycin solution were purchased from Invitrogen (NY, U.S.A).

Characterization. The structures of monomer and polymers were characterized by $^1$H NMR spectrum on a Varian 400 FT-NMR spectrometer (400.0 MHz). The molecular weight ($M_n$ and $M_w$) and polydispersity index ($M_w/M_n$) of polymers were determined by gel permeation chromatography (GPC) with a Waters 2414 refractive index detector. A series of commercial polystyrene standards were used for calibration curves. The average particle size, size distribution and morphology of micelles were measured by dynamic light scattering (DLS, Malvern Zeta Sizer) and transmission electron microscopy (TEM).

Synthesis of VD monomer. Vinylbenzyl chloride (305.2 mg, 2 mM), 4,4'-Dithiodibutyric acid (2.38 g, 10 mM) and K2CO$_3$ (0.69 g, 5 mM) were dissolved in 10 mL DMF and reacted at 50° C. under stirring. After 16 h, the mixture was cooled down to room temperature, followed by adding 80 mL of CH$_2$Cl$_2$. The mixture was centrifuged at 4500 rpm for 12 min and the supernatant was washed with water for three times, and then dried with anhydrous sodium sulfate. The VD monomer was obtained by column chromatography purification with ethyl acetate/petroleum ether (v/v, 1/2~1/1) as the elution.

Synthesis of POEG-co-PVD polymer. 4-Cyano-4-(thiobenzoylthio)pentanoic acid (6 mg, 0.0215 mmol), AIBN (2 mg, 0.0124 mmol), VD monomer (300 mg, 0.95 mmol), OEG950 monomer (400 mg, 0.42 mmol), and 2 mL of dried tetrahydrofuran were added into a Schlenk tube. After deoxygenation with three free-pump-thawing cycles, the mixture was stirred at 80° C. under the protection of N2 for 18 h. Then, the reaction was quenched by liquid nitrogen and the POEG-co-PVD polymer was obtained by precipitation in ether for 3 times. Conversion$_{(OEG950\ monomer)}$=45.9%; Conversion$_{(VD\ monomer)}$=50.0%.

Synthesis of POEG-co-PVDGEM polymer. The as-synthesized POEG-co-PVD polymer (120 mg, 0.17 mmol —COOH), GEM (179 mg, 0.68 mmol), HOBT (270 mg, 2 mmol), and EDC (450 mg, 2.35 mmol) were dissolved in 30 mL of DMSO with the addition of 300 μL of DIPEA. After stirring at 37° C. for 72 h, the mixture was dialyzed against DMSO and water for 2-3 days. The POEG-co-PVDGEM polymer was obtained after lyophilization.

Determination of GEM loading content in POEG-co-PVDGEM polymer. The GEM loading content in POEG-co-PVDGEM polymer was quantified by alkaline hydrolysis method with 1 N NaOH [32, 33]. The amount of GEM in the polymer was measured by high performance liquid chromatography (HPLC) with UV detector using methanol/water (04:96 v/v) as a mobile phase.

Preparation and characterization of drug loaded micelles. Blank and drug-loaded micelles were prepared by film hydration method. POEG-co-PVDGEM polymer and anti-cancer drugs (e.g. PTX, NLG919, DOX, Dasatinib or 10058-F4) were mixed in dichloromethane/methanol with different carrier/drug ratios. After completely removing the organic solvents, a thin film was formed, which was then hydrated with PBS solution to give PTX-loaded POEG-co-PVDGEM micelles. Micelles co-loaded with PTX and NLG were prepared in a similar way.

Drug loading capacity (DLC) and drug loading efficiency (DLE) were determined by HPLC and calculated according to the following equations:

DLC (%)[weight of drug loaded/(weight of polymer+drug used)]×100

DLE (%)=(weight of loaded drug/weight of input drug)×100

Critical micelle concentration (CMC) of POEG-co-PVDGEM micelles. The CMC values of POEG-co-PVDGEM micelles were measured using nile red as a fluorescence probe [59]. POEG-co-PVDGEM micelles (1 mg/mL) were prepared by film hydration method, and diluted into different concentrations, which were then added to each vial containing nile red. After overnight incubation, fluorescence intensities of the solutions were measured by fluorescence spectrometer.

In vitro PTX and NLG release. The PTX and NLG release from POEG-co-PVDGEM micelles were examined at 37° C. via a dialysis method. PTX/NLG co-loaded POEG-co-PVDGEM micelles was transferred into a dialysis bag with MWCO of 3500 Da, which was then incubated in 50 mL PBS with 0.5% (w/v) tween 80 under gentle shaking. At specific time intervals, the PTX and NLG concentrations in the dialysis bag were determined by HPLC.

MTT assay. The combinational effect of PTX and GEM as well as the cytotoxicity of blank and drug-loaded micelles were investigated by MTT assay using murine pancreatic carcinoma cell lines PANC02 and H7 cells. Cells were seeded into a 96-well plate at a density of 5000 cells/well and incubated in 100 μL of Dulbecco's Modified Eagle medium (DMEM) containing 10% FBS for 24 h. Cells were treated with various concentrations of free PTX, GEM or micelles solution for 96 h. Then, 20 μL of MTT solution (5 mg/mL) were added to each well and the cells were incubated for another 4 h. After removing the medium, 100 μL of DMSO were added into each well to dissolve MTT formazan crystals. The optical density was measured using a microplate reader and the cell viability was calculated with untreated cells as a control.

In vitro IDO inhibition. An IDO assay was used to evaluate the IDO inhibitory activity of drug-loaded micelles [15]. Briefly, PANC02 cells were seeded in a 96-well plate ($5 \times 10^3$ cells/well). After culturing overnight, recombinant human IFN-γ was added to each well with concentration of 50 ng/mL. Then cells were treated with various concentrations of micelles or free NLG919 for 48 h. The supernatant (150 μL) was transferred to a new 96-well plate, followed by the addition of 75 μL of 30% trichloroacetic acid. After incubation at 50° C. for 30 min, N-formylkynurenine was hydrolyzed to kynurenine. The supernatants were transferred into a new 96-well plate and treated with an equal volume of Ehrlich reagent (2% p-dimethylamino-benzaldehyde in glacial acetic acid, w/v) for 10 min for the colorimetric assay at 490 nm.

In vivo Biodistribution. DiR-loaded POEG-co-PVD micelles and PGEM micelles with a DiR concentration of 0.5 mg/mL were injected into PANC02 tumor bearing mice. At indicated time points, the mice were imaged by IVIS 200 system (Perkin Elmer, USA) at a 60 s exposure time with excitation at 730 nm and emission at 835 nm. The mice were sacrificed for imaging. The tumor and various organs were excised for ex vivo imaging.

In vivo tumor penetration. Fluorescence probe rhodamine and fluorescein was loaded into PGEM carrier and POEG-co-PVD carrier, correspondingly [60]. These nanoparticles (4 mg each) were mixed in 200 μL PBS and co-injected into the mice via the tail vein. Tumors were excised at 15 h after injection, and frozen sectioned at 7-μm thickness. The sections were stained with DAPI to label the cell nucleus. The fluorescence signal was examined under a fluorescence microscope (OLYMPUS America, Melville, NY).

In vivo therapeutic study. A syngeneic PANC02 pancreatic tumor model was established by inoculating $2 \times 10^5$ PANC02 cells into the flank of C57BL/6 mice. When the tumor volume reached around 50 mm$^3$, mice were divided into six groups (n=5) and treated with PBS, POEG-co-PVDGEM micelles, PTX/POEG-co-PVDGEM micelles, NLG/POEG-co-PVDGEM micelles, PTX/NLG/POEG-co-PVDGEM micelles, and combination of Taxol and free GEM, respectively, every three days for a total of 5 times. The dosage of GEM, PTX and NLG were kept at 20 mg/kg, 10 mg/kg and 20 mg/kg. Tumor volume and mice body weights were measured every three days. The tumor volume (V) were calculated by the formula: V=(length of tumor)×(width of tumor)$^2$/2. After the completion of the experiment, tumor tissues were excised and fixed with 10% formaldehyde, followed by embedment in paraffin. The sliced tissues at 5 μm were stained by hematoxylin and eosin (H&E) and observed under a Zeiss Axiostar plus Microscope (PA, USA).

Quantification of tumor-infiltrating lymphocytes by flow cytometry. C57BL/6 mice bearing PANC02 tumors received various treatments via i.v. administration every 3 days for 3 times. Tumors and spleen were excised at 24 h following the last treatment. Single cell suspensions were filtered and red blood cells were lysed. Then the cells were stained with various antibodies for flow cytometry analysis with FlowJo software (Tree Star Inc.).

Statistical analysis. Data are presented as mean±standard deviation (SD). The differences between groups were compared by one-way analysis of variance (ANOVA), and $p<0.05$ is considered statistically significant.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

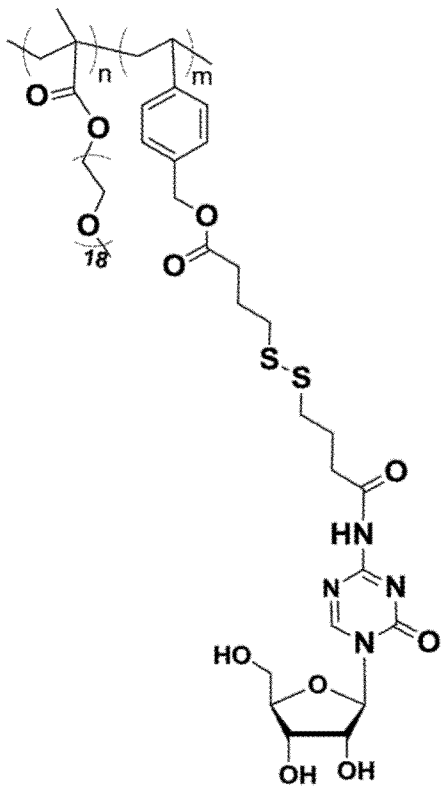

What is claimed is:

1. A polymer, comprising:
   (1) an alkylene polymer backbone,
   (2) a first plurality of pendant groups attached to the alkylene polymer backbone and comprising a therapeutic or diagnostic agent comprising a plurality of hydroxyl groups, and
   (3) a second plurality of pendant groups attached to the alkylene polymer backbone and comprising at least one hydrophilic polymer,
   wherein the first plurality of pendant groups is attached to the alkylene polymer backbone via a linking moiety comprising at least one benzyl group which is interactive via π-π stacking.

2. The polymer of claim 1, wherein the first plurality of pendant groups attached to the alkylene polymer backbone comprises a therapeutic agent.

3. The polymer of claim 2, wherein the therapeutic agent comprises a nucleoside.

4. The polymer of claim 3 wherein the nucleoside is selected from the group consisting of gemcitabine, azacytidine, and cytarabine.

5. The polymer of claim 3 wherein the nucleoside is gemcitabine.

6. The polymer of claim 1 wherein the therapeutic agent or diagnostic agent is covalently attached to the first linking moiety, via a moiety that is labile in vivo.

7. The polymer of claim 6, wherein the moiety that is labile in vivo comprises at least one of an ester bond, an orthoester bond, a thioether-ester bond, an anhydride bond, an amid bond, a carbonate bond, a disulfide bond, a hydrazone bond, a cic-acotinyl bond, an acetal bond, a carboxydimethyl maleate bond, an imine bond, an oxime bond, a silyl ether bond, a ketal bond, a thioketal bond and a protease cleavable peptide.

8. The polymer of claim 7, wherein the moiety that is labile in vivo comprises at least one of an ester bond and a disulfide bond.

9. The polymer of claim 6 wherein a plurality of the polymers forms a micelle having a diameter no greater than 50 nm.

10. The polymer of claim 1 wherein the second plurality of pendant groups is attached to the alkylene polymeric backbone via a second linking group comprising a hydrolytically labile group.

11. The polymer of claim 10 wherein the hydrolytically labile group is an ester group, an orthoester group, a thioether-ester group, an anhydride group, an amide group, or a carbonate group.

12. The polymer of claim 11 wherein the hydrolytically labile group is an ester group.

13. The polymer of claim 10, wherein the at least one hydrophilic polymer has a molecular weight in the range of from 500 Da to 2 kDa.

14. The polymer of claim 1, wherein the at least one hydrophilic polymer is selected from the group consisting of: a polyalkylene oxide, a polyvinylalcohol, a polyacrylic acid, a polyacrylamide, a polyoxazoline, a polysaccharide, and a polypeptide.

15. The polymer of claim 14, wherein the at least one hydrophilic polymer is a polyethylene glycol.

16. The polymer of claim 14, wherein the at least one hydrophilic polymer has a molecular weight in the range of from 100 Da to 5 kDa.

17. A polymer, comprising:
  (1) an alkylene polymer backbone,
  (2) a plurality of first pendant groups, comprising at least one nucleoside,
  (3) a plurality of first linking moieties, linking the first pendant groups to the alkylene polymer backbone,
  (4) a plurality of second pendant groups, comprising a polyalkylene oxide, and
  (5) a plurality of second linking moieties, linking the second pendant groups to the alkylene polymer backbone, wherein:

each first linking moiety comprises a group selected from

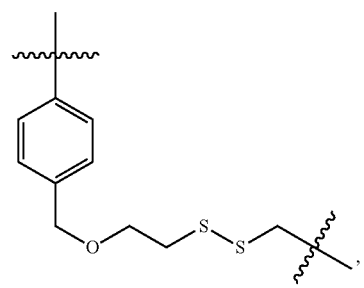

,

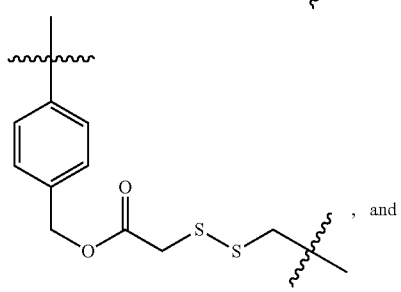

, and

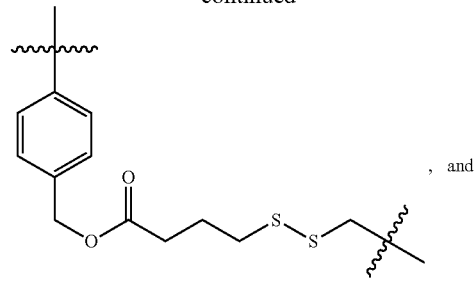

, each second linking moiety comprises a hydrolytically labile group selected from the group consisting of an ester group, an orthoester group, a thioether-ester group, an anhydride group, an amide group, or a carbonate group.

18. The polymer of claim 17, wherein the at least one nucleoside is selected from the group consisting of gemcitabine, azacytidine, and cytarabine.

19. The polymer of claim 17, wherein the at least one nucleoside is gemcitabine.

20. The polymer of claim 17 wherein the nucleoside is covalently attached to the first linking moiety via a moiety that is labile in vivo.

21. The polymer of claim 20, wherein the moiety that is labile in vivo comprises at least one of an ester bond and a disulfide bond.

22. The polymer of claim 17, wherein each second pendant group comprises polyethylene glycol (PEG).

23. The polymer of claim 22, wherein each second pendant group and second linking moiety taken together are selected from the group consisting of:

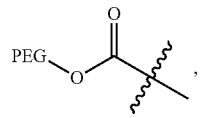

,

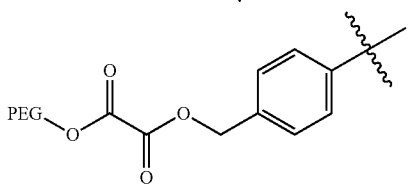

,

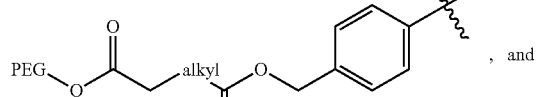

, and

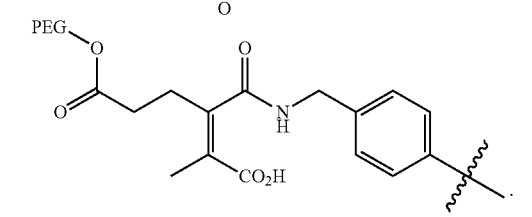

.

24. The polymer of claim 23, wherein the PEG has a molecular weight in the range of 100 Da to 5 kDa.

25. The polymer of claim 24, wherein the PEG has a molecular weight in the range of from 500 Da to 2 kDa.

26. The polymer of claim 17, which is

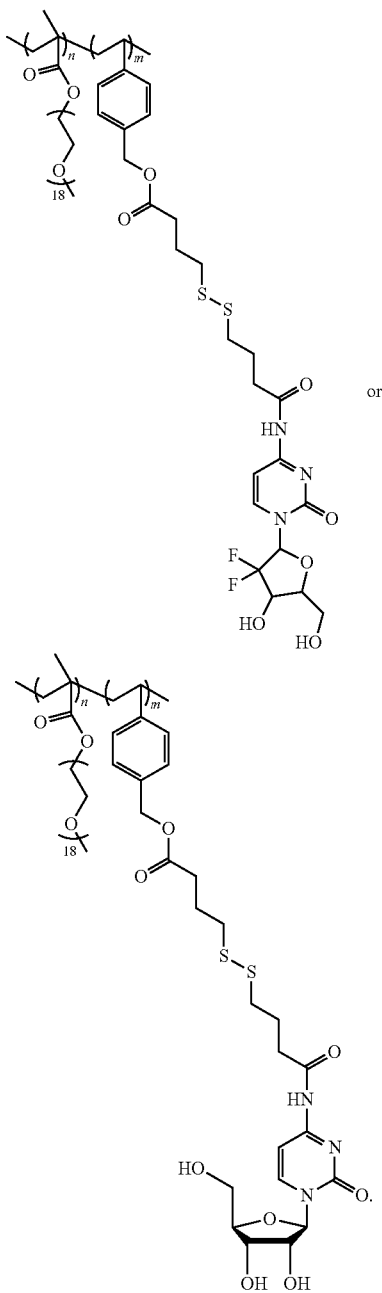

27. A formulation, comprising:
i) a plurality of polymers comprising: (1) an alkylene polymer backbone, (2) a first plurality of pendant groups attached to the alkylene polymer backbone and comprising a therapeutic or diagnostic agent comprising a plurality of hydroxyl groups, and (3) a second plurality of pendant groups attached to the alkylene polymer backbone and comprising at least one hydrophilic polymer, and
ii) at least a first compound which is a hydrophobic therapeutic compound or a hydrophobic diagnostic compound,
wherein at least one of the first plurality or the second plurality of pendant groups is attached to the alkylene polymer backbone via a linking moiety comprising at least one aryl group which is interactive via π-π stacking, and
wherein the plurality of polymers self-assemble in an aqueous environment into nanocarriers into which the first compound is loaded.

28. The formulation of claim 27 further comprising at least a second compound which is a therapeutic compound or a diagnostic compound and which is loaded into the nanocarriers.

29. The formulation of claim 28 wherein the second compound is a chemotherapeutic compound, an antiviral compound, an antibiotic compound, an antimycotic compound, an anticancer compound, an anti-rejection compound, an analgesic compound, an antioxidant compound, an immunomodulating compound, or an anti-inflammatory compound.

30. The formulation of claim 29 wherein the second compound is a small molecule therapeutic compound.

31. The formulation of claim 29 wherein the first compound and the second compound are independently selected from the group consisting of JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl)oxymethyl-5-isopropylisoxazole), rose bengal, epigallocatechin gallate, simvastatin, curcumin, indomethacin, JQ1, I-BET 151, I-BET 762, resiquimod, riluzole, tamoxifen, NLG-919 (an indoleamine 2,3-dioxygenase (IDO) pathway inhibitor), sunitinib, imatinib, erlotinib, gefitinib, cetuximab, 10058-F4(5-[(4-ethylphenyl)methylene]-2-thioxo-4-thiazolidinone), cladribine, fludarabine, nelarabine, troxacitabine, capecitabine, 2'-fluoro-2'-deoxyadenosine, acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, and 9-deazaadenosine.

32. The formulation of claim 27 wherein the first compound is a small molecule compound.

33. The formulation of claim 27 wherein the first compound is a chemotherapeutic compound, an antiviral compound, an antibiotic compound, an antimycotic compound, an anticancer compound, an anti-rejection compound, an analgesic compound, an antioxidant compound, an immunomodulating compound, or an anti-inflammatory compound.

34. The formulation of claim 33 wherein the first compound is JP4-039, paclitaxel, docetaxel, FK506 (tacrolimus), cyclosporin A, a protoporphyrin, GW4064 (3-(2,6-Dichlorophenyl)-4-(3'-carboxy-2-chlorostilben-4-yl) oxymethyl-5-isopropylisoxazole), rose bengal, epigallocatechin gallate, simvastatin, curcumin, indomethacin, JQ1, I-BET 151, I-BET 762, resiquimod, riluzole, tamoxifen, NLG-919 (an indoleamine 2,3-dioxygenase (IDO) pathway inhibitor), sunitinib, imatinib, erlotinib, gefitinib, cetuximab, 10058-F4 (5-[(4-ethylphenyl)methylene]-2-thioxo-4-thiazolidinone), cladribine, fludarabine, nelarabine, troxacitabine, capecitabine, 2'-fluoro-2'-deoxyadenosine, acyclovir, tenofovir, lamivudine, entecavir, GS-441524, GS-5734, 2'-C-methyladenosine, 7-deaza-2'-C-methyl-adenosine, 2'-C-methylguanosine, INX-08189, 2'-C-methylcytidine, 2'-C-methyluridine, 2'-C-ethynyladenosine, NITD008, NITD449, NITD203, 4'-C-azidocytidine, balapiravir, RO-9187, BCX4430, ribavirin, 6-azauridine, or 9-deazaadenosine.

35. The formulation of claim 27 wherein the first linking moiety comprises a benzyl group which is interactive via π-π stacking.

36. The formulation of claim 27 wherein the first plurality of pendant groups attached to the alkylene polymer backbone comprises a therapeutic agent.

37. The formulation of claim 36, wherein the therapeutic agent is a nucleoside.

38. The formulation of claim 37 wherein the nucleoside is selected from the group consisting of gemcitabine, azacytidine, and cytarabine.

39. The formulation of claim 27 wherein the therapeutic agent or diagnostic agent is covalently attached to the first linking moiety, via a moiety that is labile in vivo.

40. The formulation of claim 39 wherein the nanocarriers are micelles having a diameter no greater than 50 nm.

41. The formulation of claim 40 wherein the micelles have a loading capacity for the first compound of at least 4% by weight.

42. A method of formulating a composition for delivery of a first compound, which is a hydrophobic therapeutic compound or a hydrophobic diagnostic compound, comprising:
- mixing (A) a plurality of polymers comprising (1) an alkylene polymer backbone, (2) a first plurality of pendant groups attached to the alkylene polymer backbone and comprising a therapeutic or diagnostic agent comprising a plurality of hydroxyl groups, and (3) a second plurality of pendant groups attached to the alkylene polymer backbone and comprising at least one hydrophilic polymer, with (B) a plurality of the first compounds,
- wherein at least one of the first plurality or the second plurality of pendant groups is attached to the alkylene polymer backbone via a first linking moiety comprising at least one aryl group which is interactive via π-π stacking, and
- wherein the plurality of polymers self-assemble into nanocarriers in an aqueous environment into which the first compound is loaded.

* * * * *

UNITED STATES PATENT AND TRADEMARK OFFICE
CERTIFICATE OF CORRECTION

PATENT NO. : 12,083,185 B2
APPLICATION NO. : 17/284562
DATED : September 10, 2024
INVENTOR(S) : Jingjing Sun and Song Li It is certified that error appears in the above-identified patent and that said Letters Patent is hereby corrected as shown below:

In the Claims

Column 26, Claim 23, Lines 41 to 48, the formula:

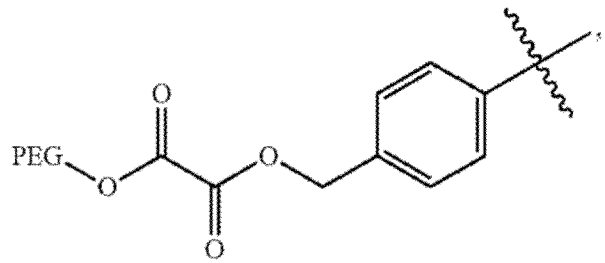

Should appear as follows:

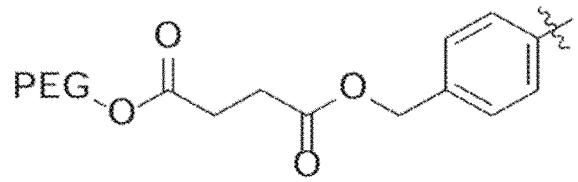

Signed and Sealed this
Third Day of June, 2025

Coke Morgan Stewart
*Acting Director of the United States Patent and Trademark Office*

CERTIFICATE OF CORRECTION (continued)
U.S. Pat. No. 12,083,185 B2

Column 27, Claim 26, Lines 28 to 52, the formula:

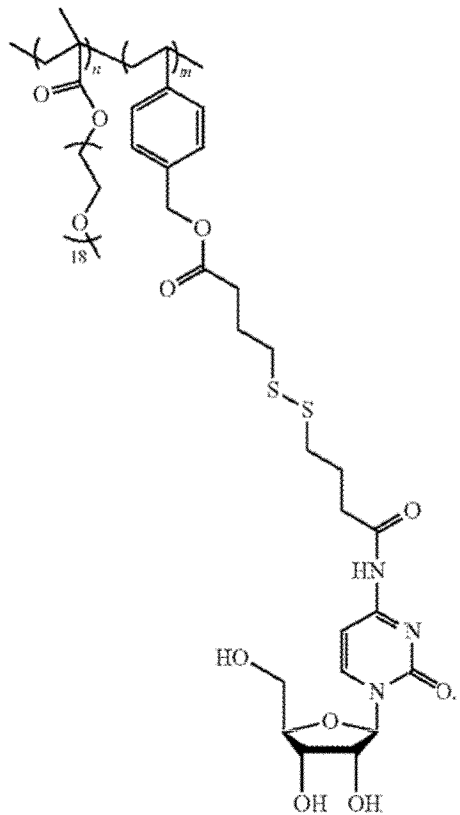

Should appear as follows: